US010361002B2

(12) United States Patent
Desai et al.

(10) Patent No.: US 10,361,002 B2
(45) Date of Patent: *Jul. 23, 2019

(54) METHOD AND APPARATUS FOR SETTING IMAGING ENVIRONMENT BY USING SIGNALS TRANSMITTED BY PLURALITY OF CLIENTS

(71) Applicant: SAMSUNG ELECTRONICS CO., LTD., Suwon-si (KR)

(72) Inventors: Nasir Desai, Suwon-si (KR); Toshihiro Rifu, Suwon-si (KR); Yeon-ju Lee, Suwon-si (KR); Jin-mo Jung, Cheongju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,804

(22) Filed: Feb. 23, 2018

(65) Prior Publication Data
US 2018/0190379 A1 Jul. 5, 2018

Related U.S. Application Data

(63) Continuation of application No. 14/468,600, filed on Aug. 26, 2014, now Pat. No. 9,904,767.

(30) Foreign Application Priority Data

Sep. 25, 2013 (KR) .................. 10-2013-0114140

(51) Int. Cl.
G16H 40/63 (2018.01)
H04N 7/15 (2006.01)
(Continued)

(52) U.S. Cl.
CPC ............ G16H 40/63 (2018.01); A61B 6/548 (2013.01); A61B 6/566 (2013.01); G06F 19/321 (2013.01);
(Continued)

(58) Field of Classification Search
CPC ...................... G16H 40/63; G06F 19/3425
(Continued)

(56) References Cited

U.S. PATENT DOCUMENTS 5,525,905 A * 6/1996 Mohapatra ........... A61B 6/0457
324/318
6,023,269 A * 2/2000 Matsuo ................. G06F 19/321
715/748
(Continued)

FOREIGN PATENT DOCUMENTS

EP  1233362 A1  8/2002
JP  2000-175870 A  6/2000
(Continued)

OTHER PUBLICATIONS

Communication dated Dec. 22, 2014 issued by the Korean Intellectual Property Office in counterpart Korean Patent Application No. 10-2013-0114140.
(Continued)

Primary Examiner — Gerald Gauthier
(74) Attorney, Agent, or Firm — Sughrue Mion, PLLC

(57) ABSTRACT

A method and apparatus for setting an imaging environment of a medical apparatus based on one or more signals transmitted from a plurality of clients are provided. The method of setting an imaging environment of a medical apparatus based on one or more signals transmitted from a plurality of clients includes transmitting information regarding an imaging operation of the medical apparatus to the plurality of clients, receiving one or more response signals
(Continued)

with respect to the information from the plurality of clients, and setting the imaging environment of the medical apparatus based on the one or more response signals.

20 Claims, 17 Drawing Sheets

(51) Int. Cl.
G06F 19/00 (2018.01)
A61B 6/00 (2006.01)
G16H 80/00 (2018.01)
G16H 30/20 (2018.01)
G16H 50/80 (2018.01)
A61B 6/03 (2006.01)

(52) U.S. Cl.
CPC ......... G06F 19/3418 (2013.01); G16H 30/20 (2018.01); G16H 50/80 (2018.01); G16H 80/00 (2018.01); H04N 7/15 (2013.01); A61B 6/03 (2013.01); A61B 6/464 (2013.01); A61B 6/465 (2013.01); A61B 6/469 (2013.01)

(58) Field of Classification Search
USPC ...... 324/318; 348/14.08, 77, 143, 74, 14.07, 348/14.09, 14.1, 211.3; 382/128, 132, 382/311, 131, 278; 705/3, 2; 709/204, 709/219, 217, 205, 231; 715/753, 748; 345/1.3, 619; 358/405; 713/168; 707/740; 725/116
See application file for complete search history.

(56) References Cited

U.S. PATENT DOCUMENTS

| | | | |
|---|---|---|---|
| 6,275,869 B1 | 8/2001 | Sieffert et al. | |
| 6,285,392 B1* | 9/2001 | Satoda ................ | H04N 7/142 348/14.08 |
| 6,477,708 B1* | 11/2002 | Sawa .................. | H04N 7/147 348/14.08 |
| 6,608,628 B1* | 8/2003 | Ross .................... | G06T 17/20 345/619 |
| 7,072,064 B2 | 7/2006 | Simpson et al. | |
| 7,106,364 B1* | 9/2006 | Noro ................... | H04N 7/15 348/14.05 |
| RE42,952 E | 11/2011 | Hu et al. | |
| 8,856,371 B2* | 10/2014 | Kariti ................. | G06Q 10/10 348/14.08 |
| 2003/0055896 A1* | 3/2003 | Hu ...................... | G06F 3/1454 709/205 |
| 2004/0260790 A1* | 12/2004 | Balloni ............... | A61B 5/055 709/219 |
| 2005/0078857 A1 | 4/2005 | Park | |
| 2006/0168532 A1 | 7/2006 | Stevens et al. | |
| 2006/0235716 A1* | 10/2006 | Mahesh .............. | G06F 19/321 709/204 |
| 2006/0235936 A1 | 10/2006 | Lei et al. | |
| 2007/0049815 A1 | 3/2007 | Sanjay-Gopal et al. | |
| 2007/0140538 A1* | 6/2007 | Doran ................. | G06F 19/321 382/128 |
| 2007/0285501 A1* | 12/2007 | Yim .................... | H04L 12/66 348/14.08 |
| 2008/0074708 A1* | 3/2008 | Mallya ............... | H04N 1/00127 358/405 |
| 2008/0194928 A1 | 8/2008 | Bandic et al. | |
| 2009/0012821 A1 | 1/2009 | Besson et al. | |
| 2009/0016641 A1* | 1/2009 | Paladini ............. | G06T 15/08 382/278 |
| 2009/0021587 A1 | 1/2009 | Snyderman et al. | |
| 2009/0060293 A1 | 3/2009 | Nagao et al. | |
| 2009/0202179 A1* | 8/2009 | Shivanna ............ | G06F 19/321 382/311 |
| 2009/0243962 A1* | 10/2009 | Hioki .................. | G06F 3/1431 345/1.3 |
| 2010/0138422 A1* | 6/2010 | Mattiuzzi ........... | G06F 19/321 707/740 |
| 2011/0002513 A1* | 1/2011 | Molinari ............. | A61B 6/12 382/128 |
| 2011/0123073 A1 | 5/2011 | Gustafon | |
| 2011/0126127 A1* | 5/2011 | Mariotti ............. | G06F 19/321 715/753 |
| 2011/0137132 A1 | 6/2011 | Gustafon | |
| 2011/0180441 A1 | 7/2011 | Bach | |
| 2011/0282686 A1* | 11/2011 | Venon ................ | G06Q 50/24 705/3 |
| 2011/0293162 A1* | 12/2011 | Pajeau ............... | G06T 5/50 382/132 |
| 2011/0302414 A1* | 12/2011 | Logan ................ | G06F 19/321 713/168 |
| 2012/0150995 A1* | 6/2012 | Kunimatsu ........ | H04L 51/16 709/217 |
| 2012/0166546 A1 | 6/2012 | Venon et al. | |
| 2012/0168774 A1 | 7/2012 | Thomas et al. | |
| 2012/0169874 A1* | 7/2012 | Thomas ............. | H04N 5/23206 348/143 |
| 2012/0177183 A1 | 7/2012 | Liu et al. | |
| 2012/0296957 A1 | 11/2012 | Stinson et al. | |
| 2012/0323605 A1* | 12/2012 | Okuyama ........... | A61B 6/463 705/3 |
| 2013/0063547 A1* | 3/2013 | Kasuya .............. | H04L 12/1813 348/14.08 |
| 2013/0208955 A1* | 8/2013 | Zhao .................. | G06F 19/321 382/128 |
| 2013/0208966 A1* | 8/2013 | Zhao .................. | G06F 9/5072 382/131 |
| 2013/0223719 A1* | 8/2013 | Ohishi ................ | A61B 6/5235 382/132 |
| 2013/0243282 A1* | 9/2013 | Sato ................... | G06F 19/321 382/128 |
| 2013/0265402 A1* | 10/2013 | Tashiro .............. | A61B 1/00016 348/74 |
| 2013/0293694 A1* | 11/2013 | Mizobe .............. | H04N 7/183 348/77 |
| 2014/0098174 A1* | 4/2014 | Summers ........... | H04N 7/15 348/14.1 |
| 2014/0181888 A1 | 6/2014 | Li et al. | |
| 2014/0376791 A1 | 12/2014 | Heigl et al. | |
| 2015/0049163 A1* | 2/2015 | Smurro .............. | H04L 65/4015 348/14.08 |
| 2015/0085066 A1* | 3/2015 | Desai ................. | A61B 6/548 348/14.08 |
| 2015/0142461 A1* | 5/2015 | Darty ................. | G06K 9/00979 705/2 |
| 2015/0201161 A1* | 7/2015 | Lachapelle ........ | H04N 7/15 348/14.07 |

FOREIGN PATENT DOCUMENTS

| | | |
|---|---|---|
| JP | 2002-301046 A | 10/2002 |
| JP | 2007-141245 A | 6/2007 |
| KR | 10-0450278 B1 | 9/2004 |

OTHER PUBLICATIONS

Communication from the Korean Intellectual Property Office dated Jun. 22, 2015 in a counterpart Korean application No. 10-2013-0114140.
Communication from the European Patent Office dated Jul. 31, 2015 in a counterpart European Application No. 14182364.1.
Communication from the Korean Intellectual Property Office dated Sep. 8, 2015 in a counterpart Korean application No. 10-2013-0114140.

* cited by examiner

FIG. 3

METHOD AND APPARATUS FOR SETTING IMAGING ENVIRONMENT BY USING SIGNALS TRANSMITTED BY PLURALITY OF CLIENTS

CROSS-REFERENCE TO RELATED APPLICATION

This application is a Continuation of U.S. patent application Ser. No. 14/468,600 filed Aug. 26, 2014, which claims priority from Korean Patent Application No. 10-2013-0114140, filed on Sep. 25, 2013, in the Korean Intellectual Property Office, the disclosures of which are incorporated herein in their entirety by reference.

BACKGROUND

1. Field

Methods and apparatuses consistent with the exemplary embodiments relate to a method and apparatus for setting a imaging environment of a medical apparatus based on at least one signal transmitted from a plurality of clients, and more particularly, to a method and apparatus for setting a imaging environment of a medical apparatus by providing a plurality of clients with information for setting the imaging environment in real-time or simultaneously and receiving at least one response signal from each of the plurality of clients.

2. Description of the Related Art

Compared to a general X-ray apparatus, a CT system provides a cross-sectional image of an object and may show an inner structure (e.g., an organ such as a kidney, a lung, etc.) of the object without any overlap with other objects.

The CT system may obtain a plurality of pieces of image data of areas with a thickness of no more than 2 mm for several tens to several hundreds of times per second and then may process the plurality of pieces of image data. Accordingly, the CT system may provide a relatively accurate cross-sectional image of the object.

That is, tomographic images of the object are captured a plurality of times while rotating an X-ray tube and an X-ray detector around the object. X-ray projection data of the object obtained through the image capturing operations may be reconstructed as cross-sectional images of the object through mathematical calculations such as an iterative method or a back-projection method.

The CT system has been developed in order to acquire high quality images within a short imaging time while at the same time reducing an amount of radiation exposure to the object.

SUMMARY

One or more exemplary embodiments include a method and apparatus for setting a imaging environment of a medical apparatus based on at least one signal transmitted from a plurality of clients.

Additional aspects will be set forth in part in the description which follows and, in part, will be apparent from the description, or may be learned by practice of the presented exemplary embodiments.

According to one or more exemplary embodiments, a method of setting an imaging environment of a medical apparatus based on one or more signals transmitted from a plurality of clients, the method includes: transmitting information regarding an imaging operation of the medical apparatus to the plurality of clients, receiving one or more response signals with respect to the information from the plurality of clients, and setting the imaging environment of the medical apparatus based on the one or more response signals.

The information regarding the imaging operation may include at least one of an image monitoring information, an imaging parameter information, and an image processing information.

The one or more response signals may include at least one of an imaging approval signal or an imaging termination signal if the information related to the imaging operation is the image monitoring information, a signal to change imaging parameters if the information related to the imaging operation is the imaging parameter information, and a signal to set an image reconstruction condition if the information related to the imaging operation is the image processing information The information relating to the imaging operation may further include information about a video conference between the plurality of clients.

The one or more response signals may include at least one of an image signal and a voice signal for the video conference.

The setting of the photographing environment may include: selecting at least one of the one or more response signals according to a priority order between the plurality of clients; and setting the imaging environment of the medical apparatus according to selected response signal.

Information representing the set imaging environment may be transmitted to the plurality of clients in real-time as transmitting the information regarding the imaging operation.

According to one or more exemplary embodiments, an apparatus configured to set a imaging environment of a medical apparatus based on one or more response signals transmitted from a plurality of clients, the apparatus includes: a transmitter configured to transmit information regarding an imaging operation of the medical apparatus to the plurality of clients; a receiver configured to receive the one or more response signals with respect to the information from the plurality of clients; and an imaging environment setter configured to set the imaging environment of the medical apparatus based on the one or more response signals.

The information relating to the imaging operation may include at least one of an image monitoring information, an imaging parameter information, and an image processing information.

The one or more response signals may include at least one of an imaging approval signal or an imaging termination signal if the information related to the imaging operation is image monitoring information, a signal to change the imaging parameters if the information related to the imaging operation is the imaging parameter information, and a signal to set an image reconstruction condition if the information related to the imaging operation is the image processing information.

The information regarding the imaging operation may further include information about a video conference between the plurality of clients.

The one or more response signals may include at least one of an image signal and a voice signal for the video conference.

The imaging environment setter may further include a selector configured to select at least one of the one or more response signals according to a priority order between the plurality of clients, and sets the imaging environment of the medical apparatus according to selected response signal.

Information representing the set imaging environment may be transmitted to the plurality of clients in real-time as transmitted the information regarding the imaging operation.

According to one or more exemplary embodiments, a non-transitory computer readable recording medium includes a program for executing the method according to the above description.

BRIEF DESCRIPTION OF THE DRAWINGS

These and/or other aspects will become apparent and more readily appreciated from the following description of the exemplary embodiments, taken in conjunction with the accompanying drawings in which:

FIG. 3 is a diagram showing an example of displaying imaging information provided to a plurality of clients, according to an exemplary embodiment;

DETAILED DESCRIPTION

Figure 1:
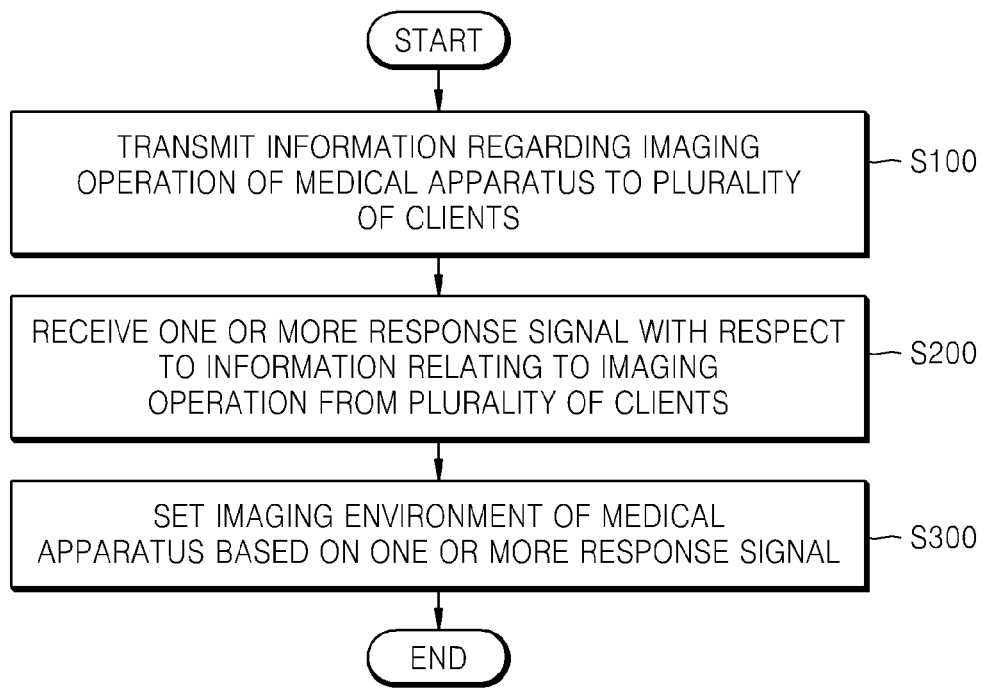
FIG. 1 is a flowchart illustrating a method of setting a imaging environment of a medical apparatus based on at least one signal transmitted from a plurality of clients, according to an exemplary embodiment.

Expressions such as "at least one of," when preceding a list of elements, modifies the entire list of elements and does not modify the individual elements of the list.

The terms used in the specification will be briefly described below, and then the exemplary embodiments will be described in detail.

The terms used in this specification are general terms currently widely used in the art in consideration of the functions, but these terms may vary according to the intention of those of ordinary skill in the art, precedents, or the occurrence of new technology in the art. Also, specified terms may be selected by the applicant, and in this case, the detailed meanings thereof will be described in the detailed description of the invention. Thus, the terms used in the specification should be understood not as simple names but according to their meanings and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

The invention now will be described more fully hereinafter with reference to the accompanying drawings, in which illustrative exemplary embodiments of the invention are shown. The exemplary embodiments may be embodied in many different forms and should not be construed as limited to the exemplary embodiments set forth herein. The exemplary embodiments are provided so that this disclosure will be thorough and complete, and will fully convey the scope of the invention to those of ordinary skill in the art. Like numbers refer to like elements throughout.

Throughout the specification, an "image" may mean multi-dimensional data formed of discrete image elements (e.g., pixels in a two-dimensional (2D) image and voxels in a three-dimensional (3D) image). For example, the image may include a medical image of an object which is captured by a computed tomography (CT) image-capturing apparatus.

Throughout the specification, a "CT image" may mean an image generated by synthesizing a plurality of X-ray images that are obtained by imaging an object while a CT image-capturing apparatus rotates around at least one axis with respect to the object.

Throughout the specification, an "object" may be a human, an animal, or a part of a human or animal. For example, the object may be an organ such as a liver, heart, womb, brain, breast, abdomen, or the like, or a blood vessel.

Also, the object may be a phantom made of a material having a volume having approximately the same density and effective atomic number of an organism. The phantom may be a sphere phantom having characteristics similar to the human body.

Throughout the specification, a "user" may be, but is not limited to, a medical expert including a medical doctor, a nurse, a medical laboratory technologist, a medial image expert, and a technician who repairs a medical apparatus.

When medical images of an object (for example, a patient) are acquired by a radiological technologist according to a clinician's prescription, the clinician determines whether the accuracy and quality of the acquired medical images are good enough for diagnosing the object. If the quality and accuracy of the acquired medical image are low and a re-imaging operation of the object is necessary, the object is inevitably exposed to further radiation.

That is, in order for the clinician to precisely diagnose a state of an organ of the patient, medical images of high quality have to be acquired. However, the shapes and locations of organs may be different according to the patient, and thus, the medical image capturing operation may have to be performed several times according to the skill of the radiological technologist. Such repeated imaging operations to acquire medical images increases the exposure time of the object to the radiation, which may be harmful to the health of the object.

Also, if the patient visits a lot of hospitals for diagnosing or treating an illness, a test (or imaging operation) that has been already performed in other hospitals may be repeatedly performed.

For example, if a patient who is suspected of having a stroke visited an emergency room of hospital A, and a few days later, visits another hospital B in order to undergo a thorough medical examination, the patient may undergo a CT scan or a magnetic resonance imaging (MRI) scan operation in hospital B after getting another CT imaging (scanning) in hospital A. If a time difference between visiting the hospital A and visiting the hospital B is short, the patient may be frequently exposed to radiation within a short period of time, and the frequent medical examinations may further deteriorate the object's health.

Also, the imaging may be performed for a plurality of times before identifying the patient's illness, or the imaging may be performed for a plurality of times within a short period of time in order to observe a treatment result.

Thus, if the radiological technologist may receive information that is necessary for diagnosis from the clinician in real-time during preparing or performing the medical image capturing operation with respect to the object, the radiological technologist may reflect the information to the imaging operation of the object so as to correct an error occurring in the imaging processes (for example, imaging a wrong portion of the object) and prevent unnecessary re-imaging process. According to the exemplary embodiments, an optimal imaging environment may be set based on participations of a plurality of users relating to the medical image capturing operation.

Also, if the plurality of users relating to the medical image capturing operation such as the radiological technologist, the clinician, et al. are located far away from each other, information for setting the imaging environment may be acquired from each of the users at the same time, and then, the medical image capturing operation is performed based on the acquired information, and thereby overcoming spatial and temporal limitations in the imaging operation.

For example, if the patient is suspected of having a stroke although no hemorrhage is observed, it is necessary to check whether a contrast or a field of view (FOV) is appropriate. In this case, the radiological technologist may adjust the contrast or the FOV for acquiring optimal images with the clinician's assistance.

Also, if the patient is suspected of having a primary bone tumor and reconstruction of the images is performed for a large thickness area, the clinician may not observe the bone precisely. Therefore, the clinician needs to reduce a thickness of a slice directly or with the radiological technologist's assistance before or during the imaging operation in order to diagnose the disease exactly.

In addition, if the medical images include much noise, a medical apparatus technician needs to apply an appropriate filter for improving image quality within a range of appropriately maintaining a good resolution of the image. The application of the filter may prevent unnecessary re-imaging operation, and thus, work amount of the radiological technologist may be reduced and clear images may be provided, and the clinician may exactly diagnose the disease.

In addition, if it is observed that the patient has a spine injury and there is a need to capture a medical image of a head portion of the patient for an exact diagnosis by the clinician, the radiological technologist may skip the imaging operation of the head portion according to clinician's opinion.

Also, the clinician may request the radiological technologist to perform a three-dimensional (3D) scanning operation for performing a CT and single-photon emission computerized tomography (SPECT) fusion operation in order to exclude Alzheimer's disease from the possible diagnostic of a patient having dementia and dysmnesia.

Also, if the patient complains of severe stomachache although there no blockage is seen in a captured image, the clinician may request the radiological technologist to perform an imaging operation using a contrast substance (for example, contrast study).

FIG. 1 is a flowchart illustrating a method of setting an imaging environment of a medical apparatus based on at least one signal transmitted from a plurality of clients, according to an exemplary embodiment.

The method of setting the imaging environment of the medical apparatus based on at least one signal transmitted from a plurality of clients according to the present exemplary embodiment may include transmitting information relating to an imaging operation of the medical apparatus to the plurality of clients (S100), receiving at least one response signal to the information about the imaging operation from the plurality of clients (S200), and setting the imaging environment of the medical apparatus based on the at least one response signal (S300).

The medical apparatus according to the exemplary embodiments may be variously referred to as medical equipment, a medical device, etc., and the medical apparatus may be an X-ray apparatus, a computed tomography (CT) apparatus, an MRI apparatus, etc. For example, a computed tomography (CT) apparatus is illustrated as a medical apparatus in FIG. 14.

The imaging environment may refer to an imaging environment regarding an imaging operation of an object, including an imaging protocol, an image recovery method, a triggering, etc.

The information about the imaging operation according to the exemplary embodiments may include at least one of image monitoring information, imaging parameter information, and image processing information.

The image monitoring information according to the exemplary embodiments may include information for observing or tracing imaging (scanning) procedures within a predetermined period. The predetermined period may be a few seconds to a few minutes or the observing or tracing may take place in real-time according to the imaging process.

The imaging parameter information according to the exemplary embodiments may include information about an imaging (or scanning) type, a tube current magnitude, a tube voltage magnitude, a start point of a region of interest, a finishing point of the region of interest, and a scanning direction. This will be described later with reference to FIG. 3.

The image processing information according to the exemplary embodiments may include information about an image recovery method, which will be described below with reference to FIG. 5.

Figure 2A:
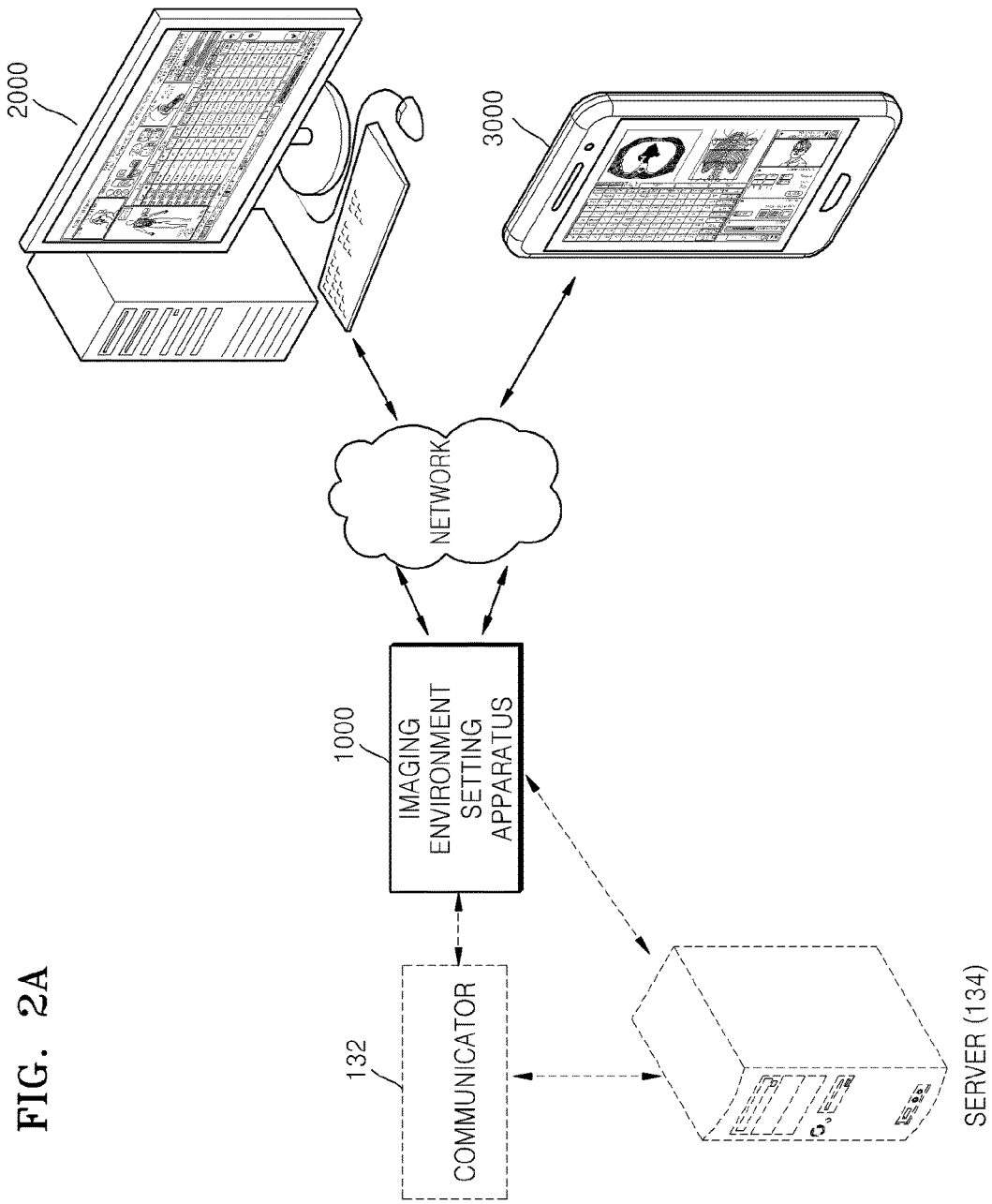
FIG. 2A is a schematic diagram illustrating the method of setting the imaging environment based on the participation of a plurality of clients, according to an exemplary embodiment.

FIG. 2A is a schematic diagram illustrating a method of setting an imaging environment of the medical apparatus based on the participation of a plurality of clients, according to an exemplary embodiment.

The plurality of clients 2000 and 3000 according to the exemplary embodiment may include a computer, a laptop computer, an electronic book terminal, a table PC, a mobile phone, a smart television (TV) having a display function, an internet protocol (IP) TV, a digital TV, a terminal for digital broadcast, a personal digital assistant (PDA), a portable multimedia player (PMP), a navigation device, a consumer electronics (CE) appliance (for example, a refrigerator or an air conditioner having a display panel), etc. However, the exemplary embodiments are not limited thereto.

According to the exemplary embodiment, an imaging environment setting apparatus 1000 may transmit information regarding an imaging operation to the plurality of clients 2000 and 3000. For example, the image monitoring information, the imaging parameter information, the image processing information, etc. may be simultaneously provided to the plurality of clients 2000 and 3000 in real-time.

The information relating to the imaging operation provided simultaneously to the plurality of clients 2000 and 3000 may be displayed in the same layout.

Otherwise, as shown in FIG. 2A, the information relating to the imaging operation provided simultaneously to the plurality of clients 2000 and 3000 may be displayed in different layouts from each other.

For example, the information relating to the imaging operation may be provided in a layout that varies depending on users, according to principal information. The image monitoring information may be principal information for a clinician, and thus, the information may be displayed based on the image monitoring information to the clinician.

Also, as described above, although the information relating to the imaging operation provided to the plurality of clients 2000 and 3000 may be initially displayed in the same layout, the layout of the information relating to the imaging operation may be changed by a user input, which will be described later with reference to FIGS. 8 and 9.

Also, the plurality of clients 2000 and 3000 may transmit at least one response signal with respect to the information relating to the imaging operation to the imaging environment setting apparatus 1000. That is, the imaging environment setting apparatus 1000 may receive at least one response signal from the plurality of clients 2000 and 3000.

The at least one response signal according to the exemplary embodiment may include at least one of an imaging approval signal and an imaging termination signal as the response signal with respect to the image monitoring information. Also, the at least one response signal may include a signal for changing the imaging parameter as the response signal with respect to the imaging parameter information. In addition, the at least one response signal may include a signal for setting an image reconstruction condition as the response signal with respect to the image processing information.

For example, the imaging environment setting apparatus 1000 may receive the imaging approval signal from the first client 2000 input from the clinician. The imaging environment setting apparatus 1000 may allow the medical apparatus to start the imaging operation according to the imaging approval signal.

Also, the imaging environment setting apparatus 1000 may notify the medical apparatus of the reception of the imaging approval signal from the first client 2000, via a communicator 132. That is, the imaging environment setting apparatus 1000 may directly communicate with the medical apparatus via the communicator 132 of the medical apparatus. Also, the imaging environment setting apparatus 1000 may indirectly communicate with the communicator 132 of the medical apparatus via a server 134.

If the imaging environment setting apparatus 1000 receives a response signal indicating that the imaging process is not satisfactory from the clinician via the first client 2000, the imaging environment setting apparatus 1000 may make the medical apparatus terminate the imaging operation. For example, when receiving a response signal from the first client 2000 which indicates that a wrong portion of an object is imaged and an imaging portion has to be changed or a response signal representing that the imaging operation has to be terminated due to bad quality, the imaging environment setting apparatus 1000 may control the medical apparatus to terminate the imaging operation.

Also, the at least one response signal according to the exemplary embodiment may include a signal for changing the imaging parameter as a response signal with respect to the imaging parameter information. The imaging parameter according to the exemplary embodiment will be described later with reference to FIGS. 3 through 7.

The imaging environment setting apparatus 1000 may receive the signal for changing the imaging parameter input from a medical apparatus technician via the second client 3000. That is, the imaging parameter that is used in the imaging operation for achieving appropriate performances, such as the acquisition of accurate images and a fast imaging speed, may be manipulated by the medical apparatus technician.

The response signal for changing the imaging parameter may be transmitted to the imaging environment setting apparatus 1000 via the second client 3000. Also, the response signal for changing the imaging parameter may be transmitted to the imaging environment setting apparatus 1000 via the first client 2000 used by the clinician.

The imaging environment setting apparatus 1000 receiving the signal for changing the imaging parameter changes the imaging parameter to correspond to the response signal, and then, controls the medical apparatus to operate according to the changed imaging parameter.

Also, the at least one response signal according to the exemplary embodiment may include a signal for setting an image reconstruction condition as a response signal with respect to the image processing information.

The imaging environment setting apparatus 1000 according to the exemplary embodiment may receive a signal for setting the image reconstruction condition input from the radiological technologist or the medical apparatus technician via the first client 2000 or the second client 3000.

That is, the response signal for setting the image reconstruction condition for acquiring images that are optimized according to the imaged portion and the imaging kind may be transmitted to the imaging environment setting apparatus 1000 via the first client 2000 or the second client 3000 by the radiological technologist or the medical apparatus technician. Also, a response signal for setting the image reconstruction condition may be transmitted to the imaging environment setting apparatus 1000 by the clinician via a predetermined client (for example, the first client 2000).

The image reconstruction condition according to the exemplary embodiment may include an algorithm based on a predetermined mathematical calculation for reconstructing an image of the object by using raw data collected via the medical apparatus. For example, the algorithm for the image reconstruction may be based on a matrix inversion method, an iterative approximation method, a back projection method, a filtered back projection method, a Fourier transformation method, and the like.

For example, a response signal for setting the image reconstruction condition according to the imaged portion, seriousness of the disease, and a kind of medical examination may be transmitted to the imaging environment setting apparatus 1000 by the clinician via a predetermined client (for example, the first client 2000).

Although the first client 2000 or the second client 3000 is the client that may be used by the clinician, the radiological technologist, and the medical apparatus technician for convenience of description, the clinician, the radiological technologist, or the medical apparatus technician may communicate with the imaging environment setting apparatus 1000 via a third client (not shown).

Also, the clinician, the radiological technologist, and the medical apparatus technician may be located within a predetermined range (for example, in the same hospital) or may be located far away from one another. As shown in FIG. 2A, the imaging environment setting apparatus 1000, the first client 2000, and the second client 3000 may communicate with each other via a network. The network may be a wired or wireless network such as a local area network (LAN), a metropolitan area network (MAN), a wide area network (WAN), a value added network (VAN), an integrated service digital network (ISDN), an Intranet, an Extranet, and a broadcasting network.

Figure 2B:
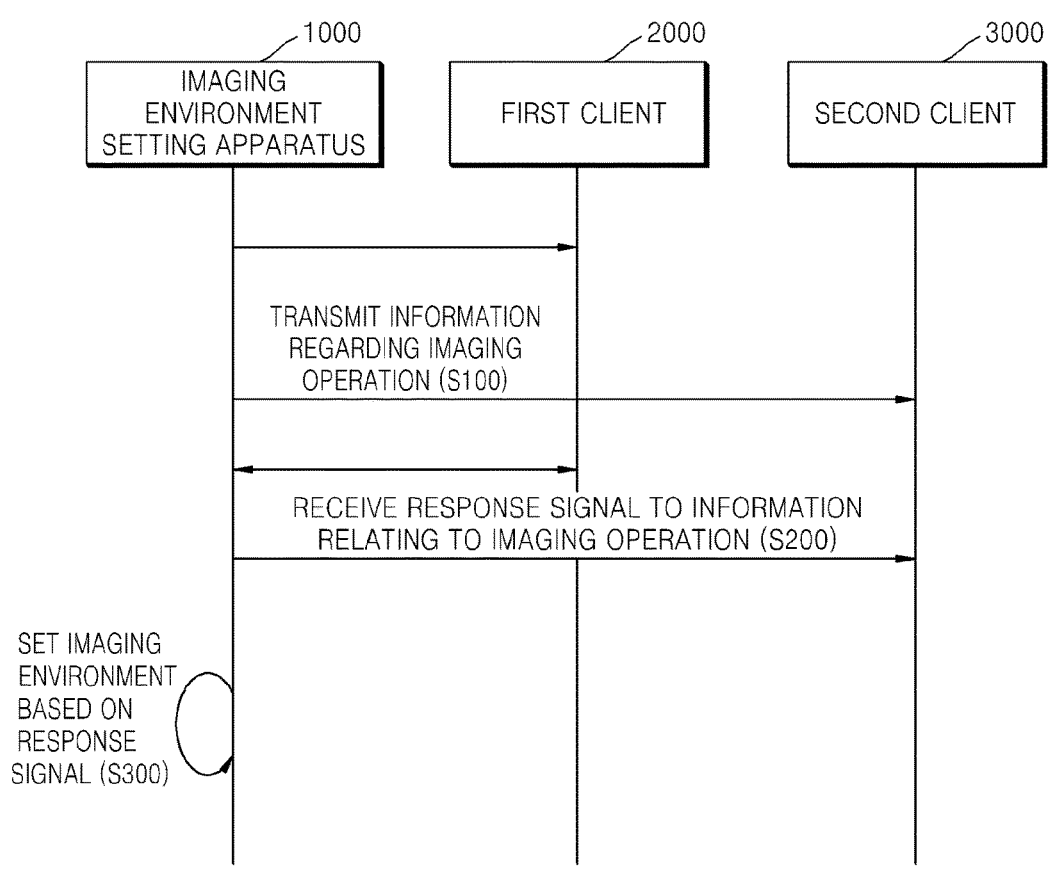
FIG. 2B is a timing diagram showing the method of setting the imaging environment based on at least one signal transmitted from a plurality of clients, according to an exemplary embodiment.

FIG. 2B is a timing diagram illustrating the method of setting the imaging environment of the medical apparatus based on the at least one signal transmitted from the plurality of clients, according to the exemplary embodiment.

The imaging environment setting apparatus 1000 may transmit the information relating to the imaging operation to at least one of the first client 2000 and the second client 3000 (S100). The information relating to the imaging operation may be simultaneously transmitted to the at least one of the first client 2000 and the second client 3000.

Also, the imaging environment setting apparatus 1000 may receive at least one response signal with respect to the information relating to the imaging operation from at least one of the first and second clients 2000 and 3000 (S200). The response signal may be the imaging approval signal, the imaging termination signal, the signal for changing the imaging parameter, and the signal for setting the image reconstruction condition, as described above.

The imaging environment setting apparatus 1000 may set the imaging environment of the medical apparatus based on the response signal (S300).

Also, information representing the set imaging environment may be transmitted to the plurality of clients in real-time as information relating to the imaging operation. That is, information including the changed imaging parameter may be transmitted to the plurality of clients simultaneously. Therefore, the plurality of clients may be informed about a state of setting the imaging environment in real-time.

Figure 3:
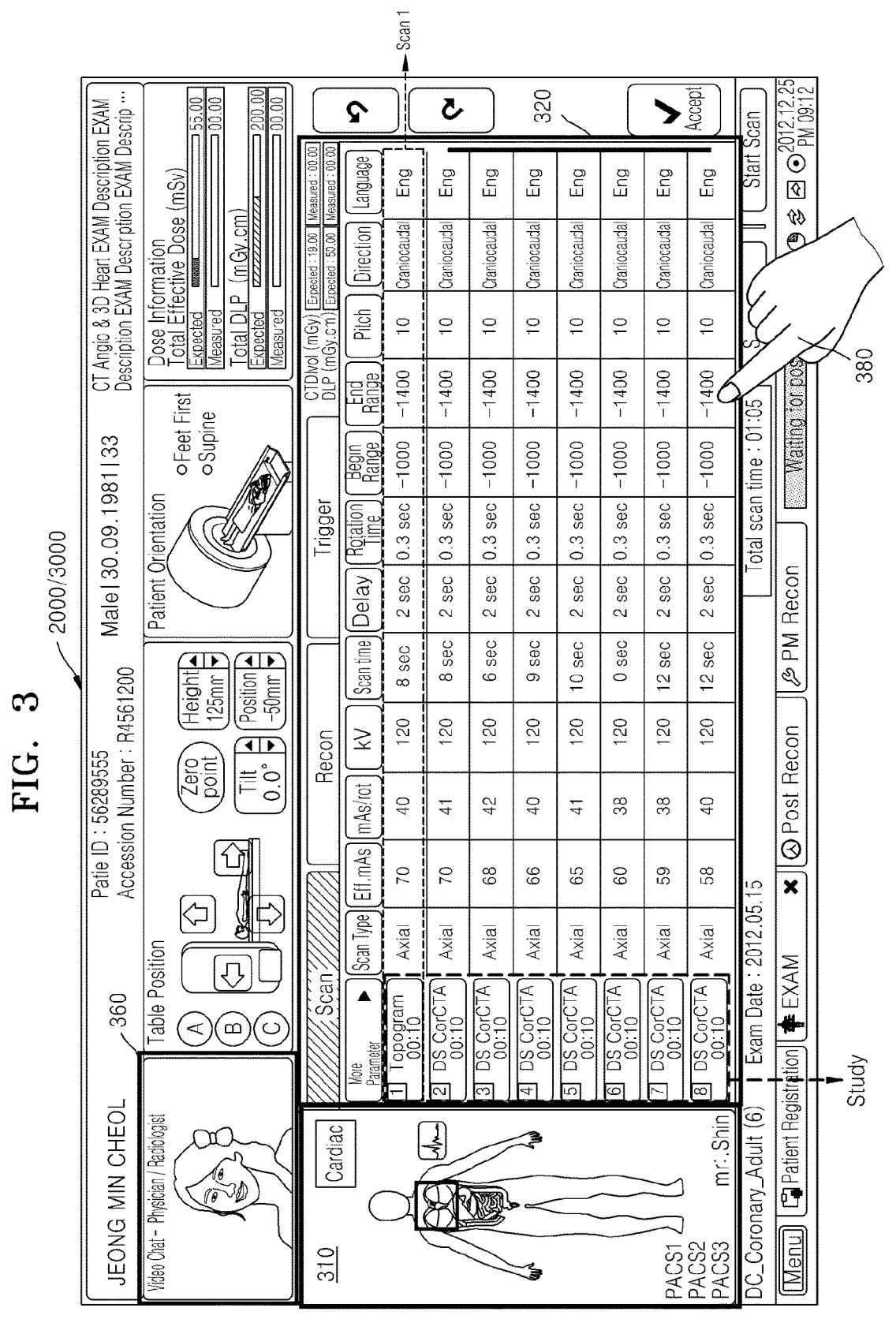

FIG. 3 is a diagram showing an example of displaying information relating to the imaging operation provided to the plurality of clients, according to the exemplary embodiment.

According to the exemplary embodiment, the information relating to the imaging operation provided to the plurality of clients may include image monitoring information 310 and imaging parameter information 320.

Also, the information relating to the imaging operation may further include information 360 about a video conference between the plurality of clients.

Also, the at least one response signal that may be transmitted to the imaging environment setting apparatus 1000 from the plurality of clients 2000 and 3000 may include at least one of an image signal and a voice signal for the video conference between the plurality of clients 2000 and 3000.

For example, the clinician using the first client 2000 may have a video conference with the medical apparatus technician by using the second client 3000 via the imaging environment setting apparatus 1000 for diagnosing the object (for example, the medical image capturing). That is, the imaging environment setting apparatus 1000 receives at least one of the image signal and the voice signal for the video conference from the first client 2000 and transmits the received signal to the second client 3000, and also receives at least one of the image signal and the voice signal from the second client 3000 and transmits the received signal to the first client 2000 so that the video conference may take place between the first client 2000 and the second client 3000.

As described above, the information relating to the imaging operation including the information about the video conference may be transmitted to the first client 2000 and second client 3000 via the imaging environment setting apparatus 1000.

The information relating to the imaging operation provided from the imaging environment setting apparatus 1000 may be respectively displayed on the first client 2000 and the second client 3000 as shown in FIG. 3.

According to the exemplary embodiment, when preparing to image the object (for example, before starting the imaging) or when performing the imaging operation of the object, the clinician, the radiological technologist, or the medical apparatus technician may hold a video conference in real-time via the imaging environment setting apparatus 1000, and thus, opinions may be shared freely. Therefore, if the clinician, the radiological technologist, and the medical apparatus technician are located far from each other, the inconvenience due to difficult communication between them may be avoided.

Also, according to the exemplary embodiment, the imaging environment may be set in real-time through cooperation between the plurality of clients, and thus, an error during the imaging operation (for example, imaging a wrong portion) may be prevented, and unnecessary processes may be omitted (for example, reduction of a field of view (FOV)), and thereby reducing a time taken to perform the imaging operation.

As shown in FIG. 3, the image monitoring information 310 may include information about a body state of the object, and information about medical images of the object, which are obtained when starting the imaging operation.

Also, the imaging parameter information 320 may be provided as, for example, a table (or matrix) including predetermined columns and rows. For example, as shown in FIG. 3, a list of available imaging items including at least one imaging protocol (for example, scan 1, etc.) about the object may be respectively provided to the plurality of clients. The available imaging items may be referred to as a study for a diagnosis.

When preparing the imaging of the object or when performing the imaging of the object, a signal for changing the imaging parameter information 320, which is generated by a user input to the first client 2000, may be transmitted to the imaging environment setting apparatus 1000.

For example, the signal for changing the imaging parameter information 320 may be generated in the first client 2000 based on a user input 380 to the first client 2000.

The user input 380 may be input to the first client 2000 or second client 3000 via an external input receiver (not shown) of the first client 2000 or second client 3000. The above user input 380 may include gestures of the user with respect to the external input receiver (not shown) of the first client 2000 or second client 3000.

The external input receiver (not shown) of the first client 2000 or second client 3000 may include a keyboard, a jog wheel, a joystick, a button, a mouse, and a touch pad. Also, if the touch pad and a display (not shown) of the first client 2000 or second client 3000 form a layered structure, the structure may be referred to as a touch screen.

For example, the display (not shown) of the first client 2000 or second client 3000 may form a layered structure to configure a touch screen. In this case, the display of the first client 2000 or second client 3000 may be used as an input device and the output device. The display may include at least one of a liquid crystal display (LCD), a thin film transistor-liquid crystal display (TFT-LCD), an organic light emitting diode (OLED), a flexible display, and a three-dimensional (3D) display.

For example, a signal for changing the imaging parameter information 320 may be generated in the first client by a tap gesture of the user with respect to the imaging parameter information 320 displayed through the first client 2000.

The tap may refer to an operation of touching the touch screen of the first client 2000 or second client 3000 fast by using a finger or a touch tool (for example, a touch pen, a stylus pen, etc.). For example, a difference between a touch-in point at which the finger or the touch tool contacts the touch screen and a touch-out point at which the finger or the touch tool separates from the touch screen is very short.

For example, a signal for changing a parameter of an image end range from −1400 to −1200 or −1600 may be generated in the first client 2000 by the tap gesture on the first client 2000.

For example, when the clinician taps (first tap) a parameter about the imaging end range currently displayed as −1400 through the first client 2000, an available range (for example, −1100 through −2000) that may be set as a new imaging end range may be displayed as a pop-up window overlapping the currently displayed information 320. Then, the clinician taps (second tap) a parameter value of a desired imaging end range in the available range to select the parameter value as a changed target parameter. Then, the first client 2000 may generate a signal for requesting the imaging environment setting apparatus 1000 to change the parameter of the imaging end range to the selected parameter value. The signal generated by the first client 2000 may be transmitted to the imaging environment setting apparatus 1000 as a response signal to the information relating to the imaging operation.

The generation of the signal for changing the image parameter is an example. Candidate values of the new parameter value at the imaging end range may be changed and displayed sequentially as −1400 to a −1500, −1600, to −2000, −1100, −1200 according to the repeated tap operations of the user. The user may select the desired parameter value by performing the tap operation repeatedly on the parameter, and the signal for changing the imaging parameter to the selected parameter may be generated in the client and may be provided to the imaging environment setting apparatus 1000.

Also, the signal for changing the imaging parameter according to the exemplary embodiment may be generated in the first client 2000 by, for example, a drag-and-drop gesture of the user using the first client 2000.

The drag-and-drop operation is an operation where the user drags and drops an item at a predetermined location on the screen by using a finger or a touch tool.

For example, the user may designate an imaging range having a predetermined size at a predetermined location on a scout image by the drag and drop gesture. The region having the predetermined size at the predetermined location may have a polygonal shape such as, for example, a square or a rectangle.

The imaging parameter information 320 according to the exemplary embodiment may include information about a scanning type, a tube current magnitude, a tube voltage magnitude, a start point of a region in interest, an end point of the region in interest, a pitch value, a scanning direction, language (for example, language that may be used in an aural description provided through a broadcasting system during the scanning operation).

Figure 4A:
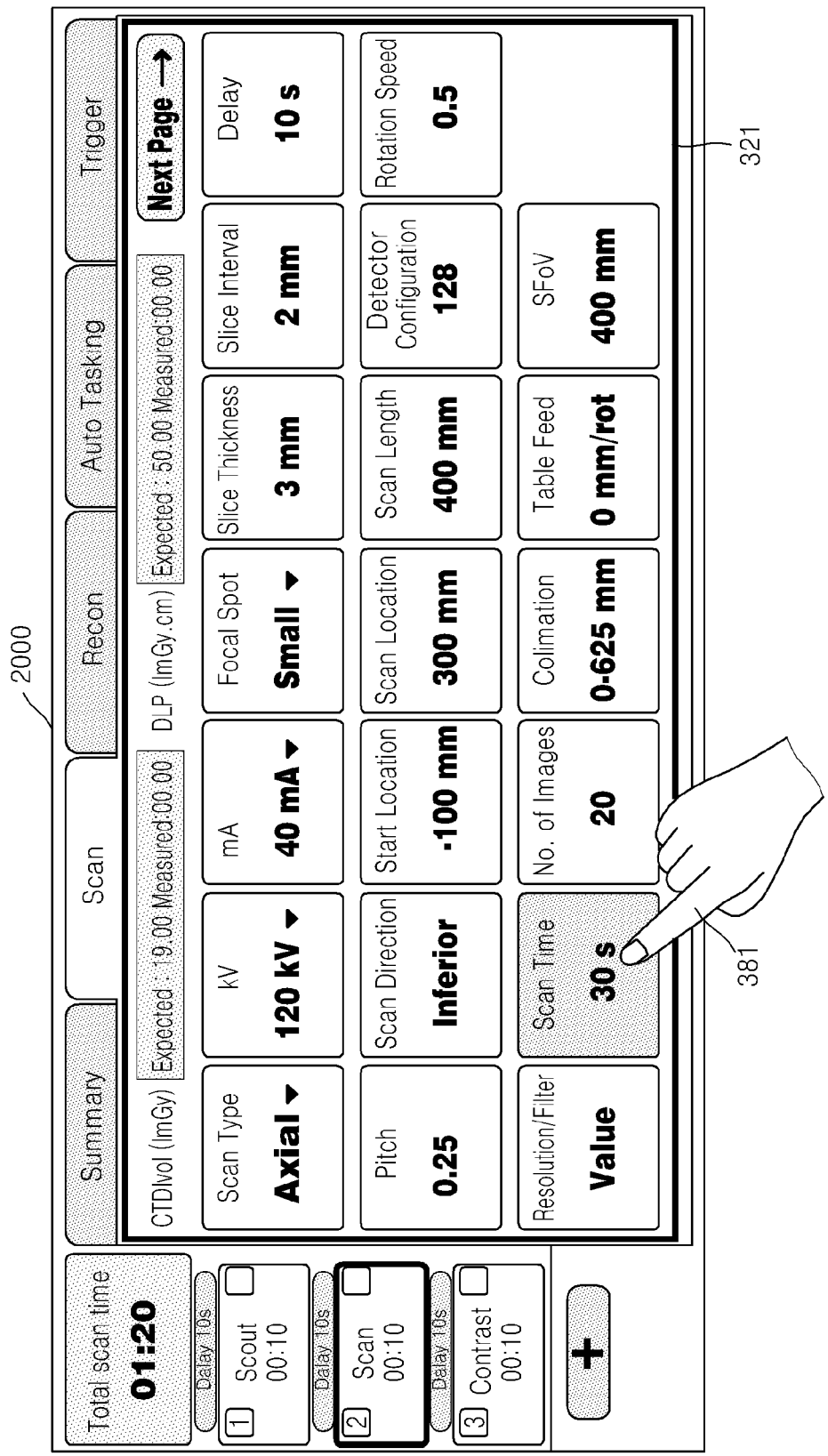
FIG. 4A is a diagram showing an example of displaying imaging parameter information provided to a plurality of clients, according to an exemplary embodiment.

FIG. 4A is a diagram showing an example of displaying the imaging parameter information provided to a plurality of clients, according to the exemplary embodiment.

For example, if the user of the first client 2000 selects a scan that is one of a list including available image items (for example, study shown in FIG. 3), detailed parameter information 321 relating to the selected scan item may be displayed on the first client 2000 as shown in FIG. 4A.

The first client 2000 may generate a signal for changing the imaging parameter information based on a predetermined input 381 of the user of the first client 2000. For example, a signal for reducing a scan time from 30 seconds to 20 seconds or increasing to 40 seconds may be generated according to a predetermined input 381 of the user.

Figure 4B:
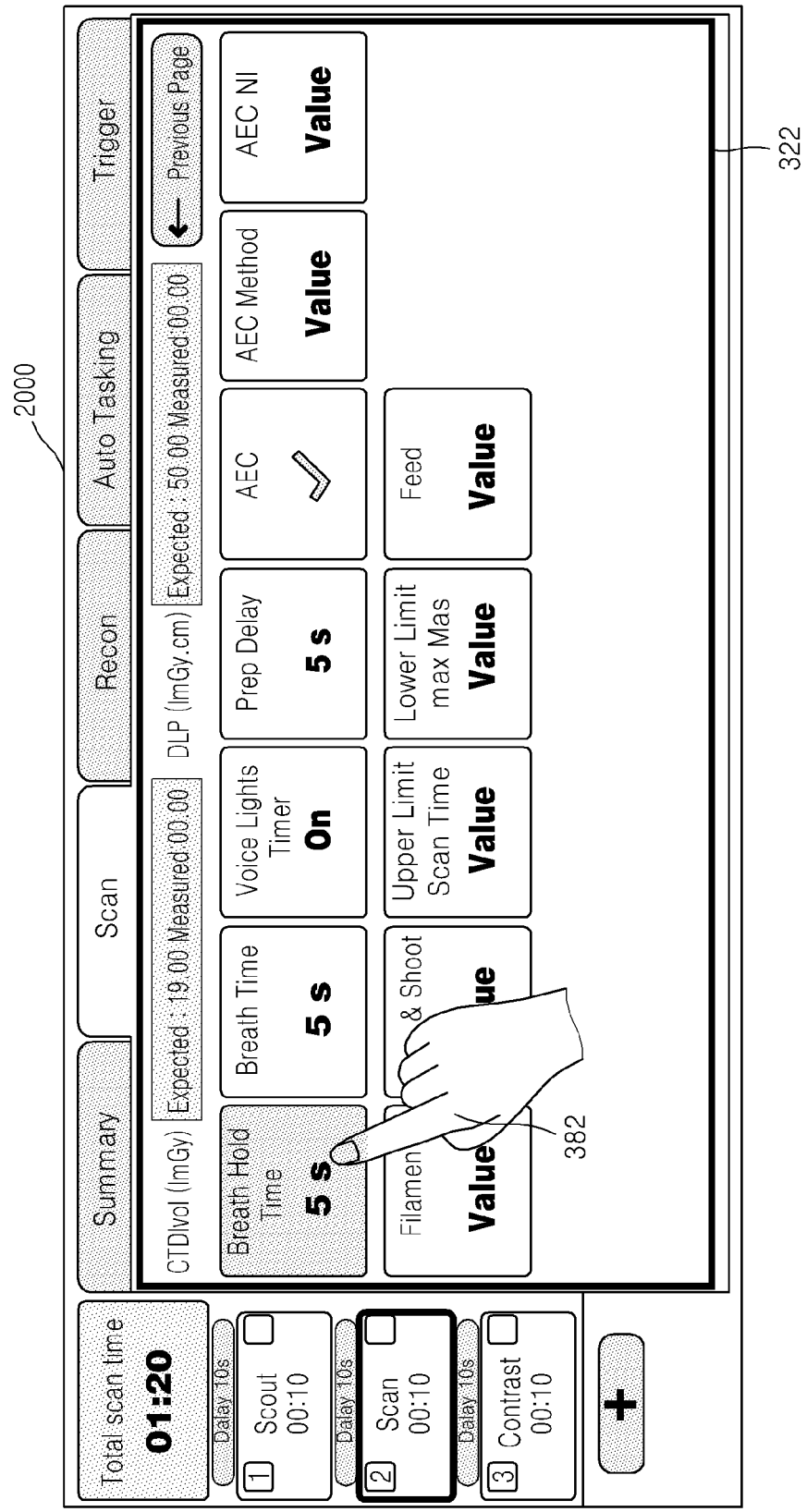
FIG. 4B is a diagram showing another example of displaying the imaging parameter information provided to a plurality of clients, according to an exemplary embodiment.

FIG. 4B is a diagram showing another example of displaying the imaging parameter information provided to the plurality of clients, according to the exemplary embodiment.

In the previous example, another detailed information 322 relating to the selected scan item may be displayed on the first client 2000 as shown in FIG. 4B.

A signal for changing a breath hold time of the patient may be generated based on a predetermined input 382 input by the user of the first client 2000. For example, the signal for reducing the breath hold time from 5 seconds to 3 seconds or increasing to 8 seconds may be generated according to the predetermined input 382. Since a child generally has a shorter breath hold time than an adult, it is important to set the imaging environment suitable for a patient in consideration of age, breath capacity, a respiratory, or the like.

For example, even if the radiological technologist fails to notice the breath capacity checking operation of the patient while setting the imaging environment, the clinician, that is the user of the first client 2000, may double-check (or feedback) the setting, and thus, an error that may be generate during the imaging process (for example, spread of the imaged image due to a failure of the breath hold) may be reduced.

The detailed information 321 and 322 of the imaging parameter may be displayed as an entire screen on the display (not shown) of the first client 2000, as shown in FIGS. 4A and 4B. When the detailed information 321 and 322 is displayed as the entire screen, the entire screen may be changed through a screen change (for example, selecting of a next page or a previous page).

Also, the detailed information 321 and 322 of the parameter may be displayed at the same time on the display (not shown) of the first client 2000 according to a predetermined screen arrangement (for example, a checkerboard type).

Figure 5:
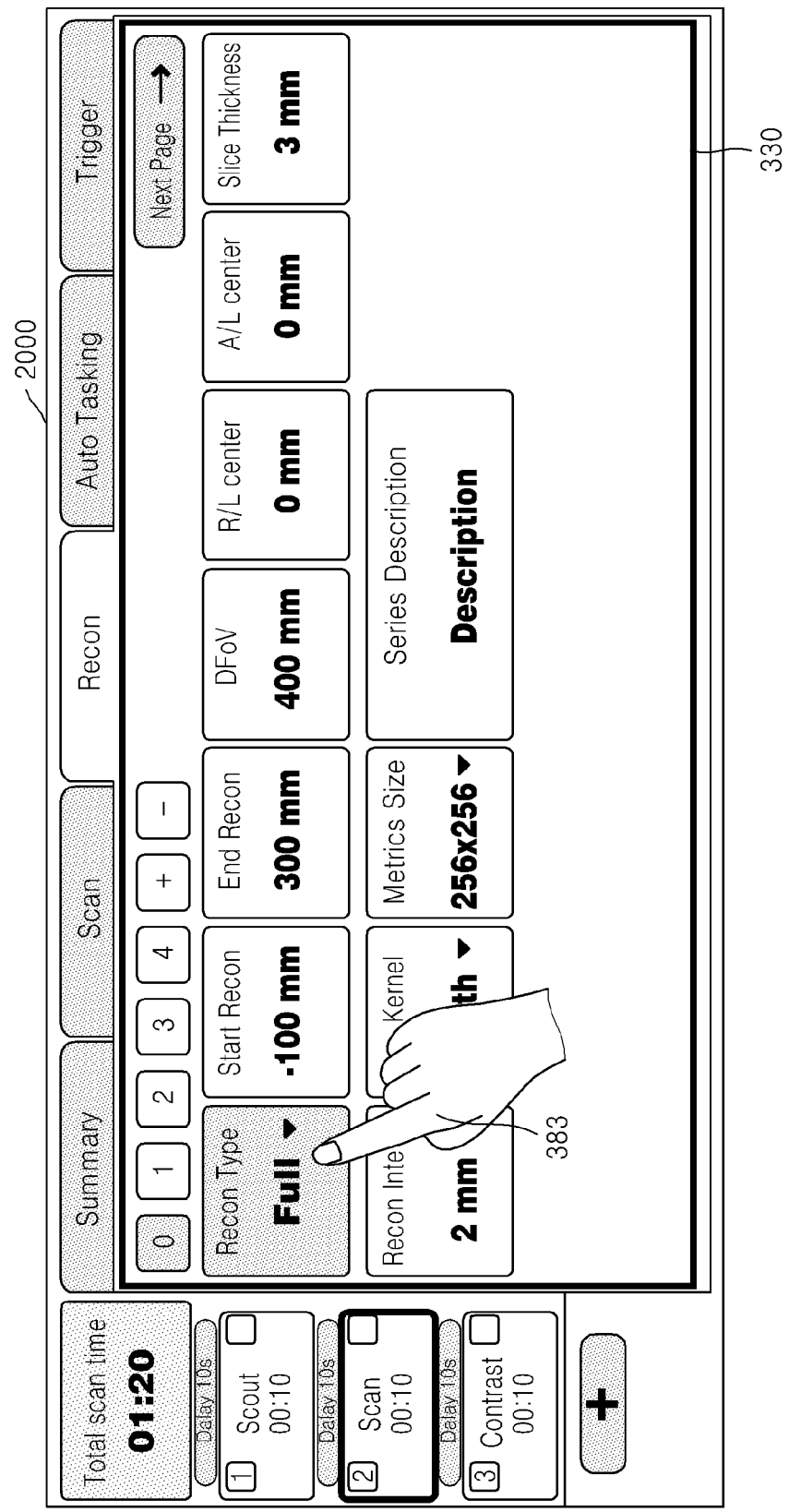
FIG. 5 is a diagram showing an example of a method of recovering an image provided to a plurality of clients, according to an exemplary embodiment.

FIG. 5 is a diagram showing an example of displaying an image reconstruction method that is to be used by the plurality of clients, according to the exemplary embodiment.

As shown in FIG. 5, detailed information 330 about an image reconstruction method provided from the imaging environment setting apparatus 1000 may be displayed on the first client 2000 or the second client 3000.

The detailed information 330 about the image reconstruction method may include additional information such as an image reconstruction type (Recon type), an image reconstruction start point (Start Recon), an image reconstruction end point (End Recon), a size of a imaged region to be displayed (DFoV), center information (R/L center, A/P center), a slice thickness, an image reconstruction interval (Recon Interval), an image reconstruction kernel (for example, image reconstruction filter) (Kernel), a measuring reference size (Metrics Size), and series description.

For example, a signal for setting image reconstruction conditions may be generated based on a user input 383 applied by the user of the first client 2000. The image reconstruction conditions may include all or some of the detailed information 330 about the image reconstruction method, which is described above.

The user of the first client 2000 or second client 3000 may set a full mode or a plus mode as the image reconstruction type (Recon type). The full mode is a mode in which a slice thickness that is determined in advance is maintained during the image reconstruction. Also, the plus mode is a mode in which a thicker slice than the slice thickness determined in advance is provided during the image reconstruction. Noise in the image according to the plus mode may be less than that in the full mode.

In the exemplary embodiment, the user of the first client 2000 may apply a predetermined input 383 to the first client 2000 in order to change the image reconstruction type, and the first client 2000 may generate a signal for setting the image reconstruction conditions including the image reconstruction type according to the user input 383. The signal generated by the first client 2000 may be transmitted to the imaging environment setting apparatus 1000 as a response signal with respect to the information relating to the imaging operation.

Figure 6:
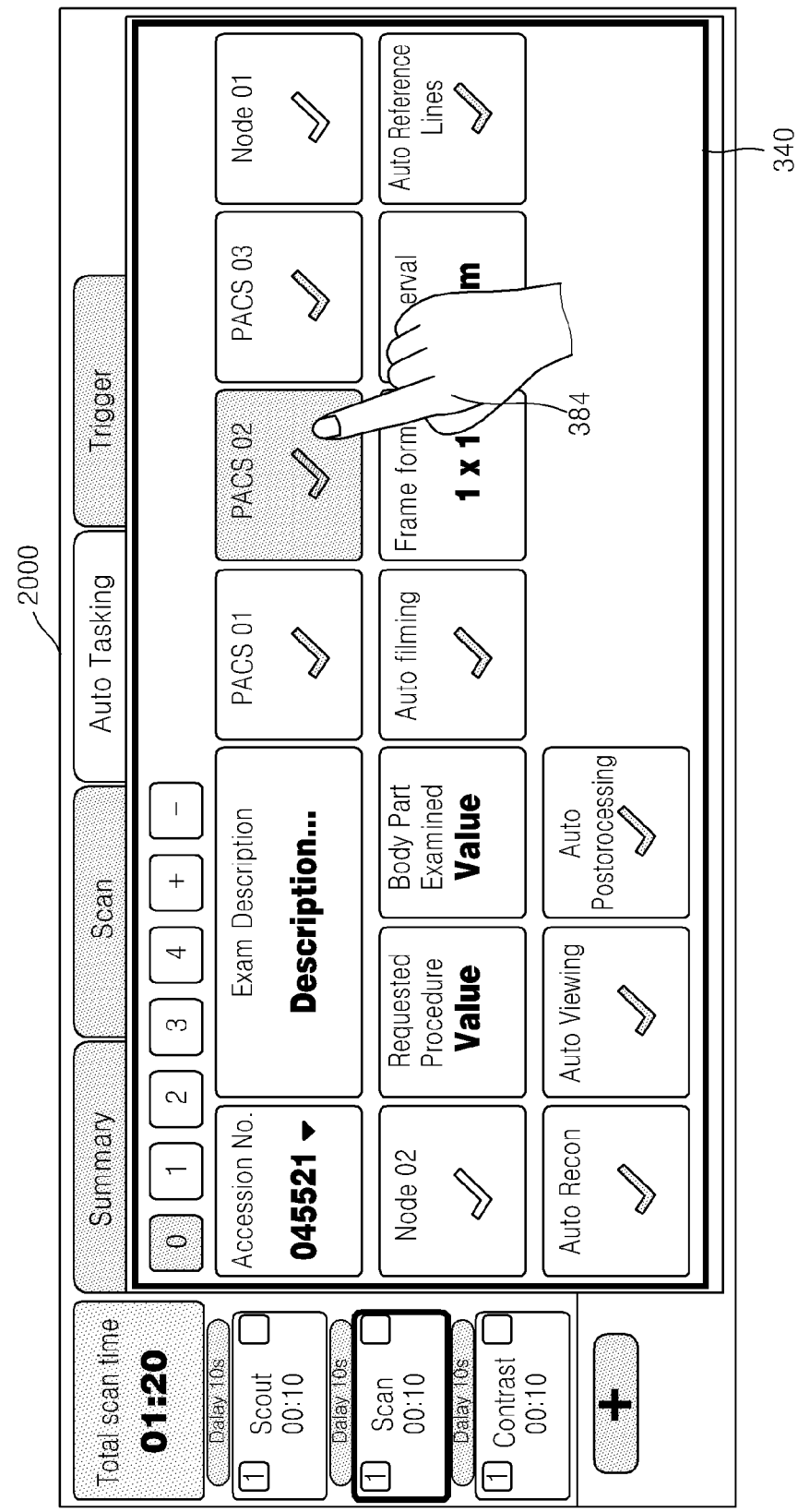
FIG. 6 is a diagram showing an example of displaying information about an operating type of a medical apparatus, which is set in advance, according to an exemplary embodiment.

FIG. 6 is a diagram showing an example of displaying information about an operation type of a medical apparatus set in advance, according to the exemplary embodiment.

According to the exemplary embodiment, the medical apparatus may operate in the imaging environment that is set in advance. As shown in FIG. 6, the medical image imaging environment may be set in advance according to a distinct indicator (for example, 045521) allocated to the disease in advance. The imaging environment set in advance may be referred to as auto tasking. Also, information about the imaging environment set in advance (340) as shown in FIG. 6 may be provided to the plurality of clients.

For example, raw data about the object, server information (for example, Picture Archiving and Communication System (PACS)) for managing reconstructed image data (for example, processing, editing, and storing data), a frame format, and an image reconstruction type may be set in advance as defaults.

The user of the first client 2000 may want to change the imaging environment according to the status of the object (for example, degree of the disease, etc.). According to the exemplary embodiment, the user of the first client 2000 may apply a predetermined input 384 to the first client 2000, and the first client 2000 may generate a signal for changing the imaging environment that is set in advance according to the application of the user input 384.

For example, according to a predetermined user input 384 for selecting a second server (for example, PACS 02), a signal for changing the server for managing the raw data of the object and the reconstructed image data from a basic server to the second server (for example, PACS 02) may be generated. The basic server may be a first server (for example, PACS 01) that is set as a default in advance.

Figure 7:
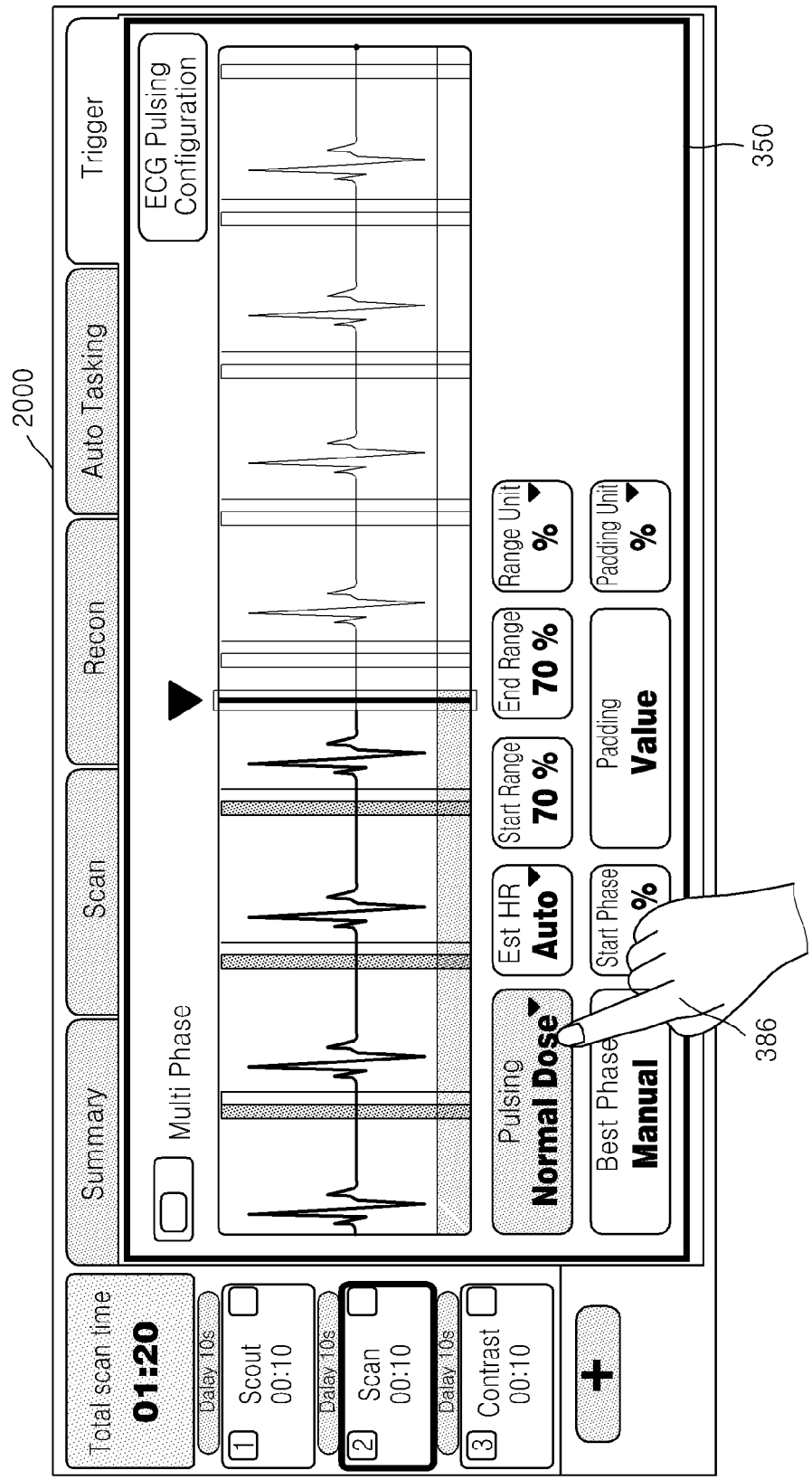
FIG. 7 is a diagram showing an example of triggering information provided to a plurality of clients, according to an exemplary embodiment.

FIG. 7 is a diagram showing an example of displaying triggering information provided to a plurality of clients, according to the exemplary embodiment.

For example, an electrocardiogram (ECG) pulse may be used to acquire medical images of a heart of the patient. According to the exemplary embodiment, the information regarding the imaging may include triggering information 350 including information about the ECG pulse. The information about the ECG pulse may be formed as a waveform having a predetermined period as shown in FIG. 7, and may be provided to the plurality of clients at the same time.

The user of the first client 2000 may change an intensity of radiation that is to be irradiated to the patient based on biological information of the patient, diagnosis history, and information about the ECG pulse. For example, if the intensity of the radiation is currently set as a normal dose and the patient is a child who had other X-ray investigations a few days before the current imaging operation, the intensity of the radiation can be made to be lower than the normal dose unless the image quality is degraded.

Also, if the intensity of the radiation is currently set as a normal dose, an adult patient who has no history of imaging and is suspected to have a small tumor small which has to be imaged precisely, the intensity of radiation has to be higher than the normal dose within a range of a maximum exposure dose to the radiation.

Therefore, in the above examples, the user of the first client 2000 applies a predetermined input 386 to the first client 2000 in order to change the intensity of the radiation, and the first client 2000 may generate a signal for changing the radiation intensity according to the application of the user input 386. The signal generated by the first client 2000 may be transmitted to the imaging environment setting apparatus 1000 as a response signal with respect to the information regarding the imaging operation.

Figure 8:
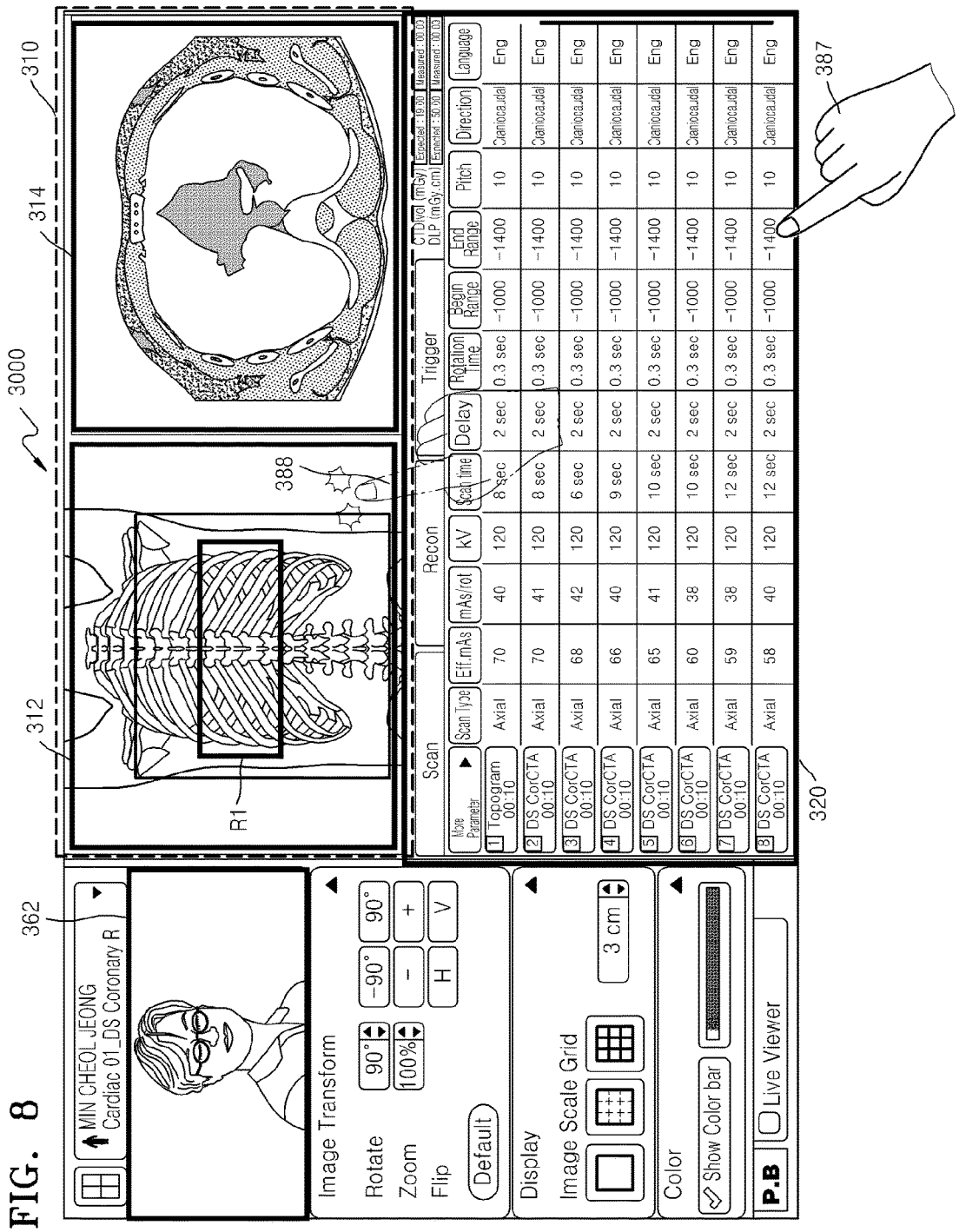
FIG. 8 is a diagram showing an example of displaying information in a client provided with information relating to the imaging, according to an exemplary embodiment.

FIG. 8 is a diagram showing an example of displaying information on a client that is provided with information regarding the imaging operation, according to the exemplary embodiment.

The second client 3000 may receive image monitoring information 310, the imaging parameter information 320, and video conference information 362 as the information relating to the imaging operation from the imaging environment setting apparatus 1000.

The image monitoring information 310 according to the exemplary embodiment may include an image 312 having a predetermined indicator R1 representing a region to be imaged or field of view (FOV) and a captured image 314 acquired corresponding to the indicator R1, as shown in FIG. 8. The captured image 314 may be sequentially displayed according to the imaged time to correspond to the slices included in the region to be imaged (FOV).

Also, a signal for changing the image parameter information 320 may be generated by a user input 387 input to the second client 3000 and may be transmitted to the imaging environment setting apparatus 1000. That is, as described above with reference to FIGS. 3 through 7, the signal for setting the imaging environment generated by the second client 3000 may be transmitted to the imaging environment setting apparatus 1000 as a response signal.

In addition, the video conference information 362 may include image information about the user of the first client 2000. That is, the user of the second client 3000 may perform a video conference with the user of another client by using the video conference information 362.

The image monitoring information 310 may be displayed on the second client 3000 in various ways by a predetermined user input 388 input to the second client 3000, which will be described below with reference to FIG. 9.

Figure 9:
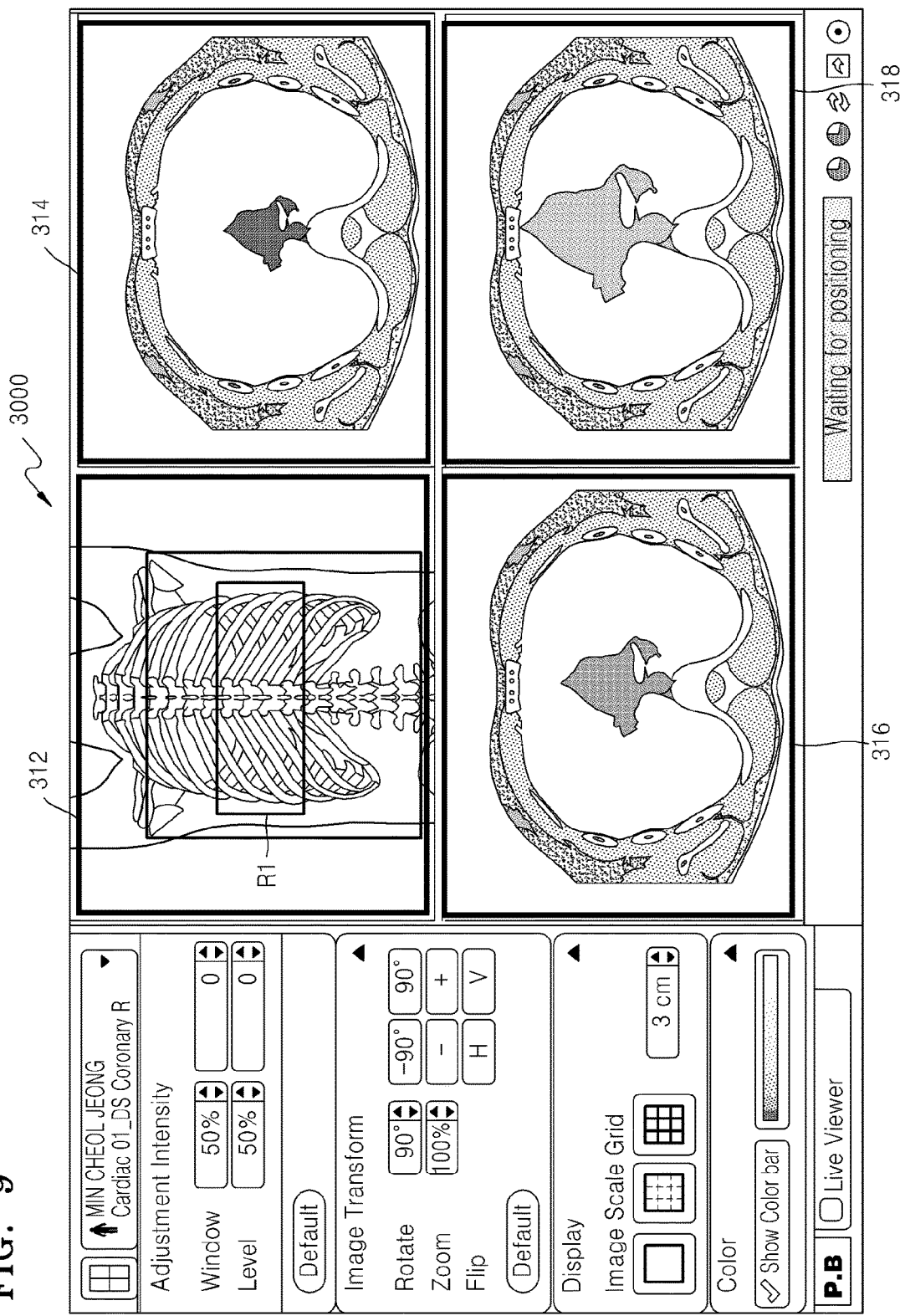
FIG. 9 is a diagram showing another example of displaying information in a client provided with the information relating to the imaging, according to an exemplary embodiment.

FIG. 9 is a diagram showing an example of displaying information on a client provided with the information relating to the imaging operation, according to the exemplary embodiment.

For example, as shown in FIG. 9, captured images 314, 316, and 318 acquired corresponding to the indicator R1 may be displayed together by a user input applied to the image 312 including the indicator R1 representing the region to be imaged (FOV) or the captured image 314 acquired to correspond to the indicator R1.

The user input 388 may include an external input applied to the client for a predetermined number of times. For example, the user input 388 may be a double tap input. The double tap denotes an operation of touching the touch screen twice rapidly by using the finger or the touch tool (for example, a stylus pen).

For example, according to the user input 388 to the second client 3000 with respect to the image 312 or 314, the second client 3000 may display a screen shown in FIG. 9 from the screen shown in FIG. 8. When the CT imaging operation is performed, one or more captured images 314, 316, and 318 may be acquired according to the slices or specific areas included in the region to be imaged (FOV). The one or more captured images 314, 316, and 318 may be displayed on the display of the second client 3000 as shown in FIG. 9. The one or more captured images 314, 316, and 318 may be displayed in real-time.

Figure 10:
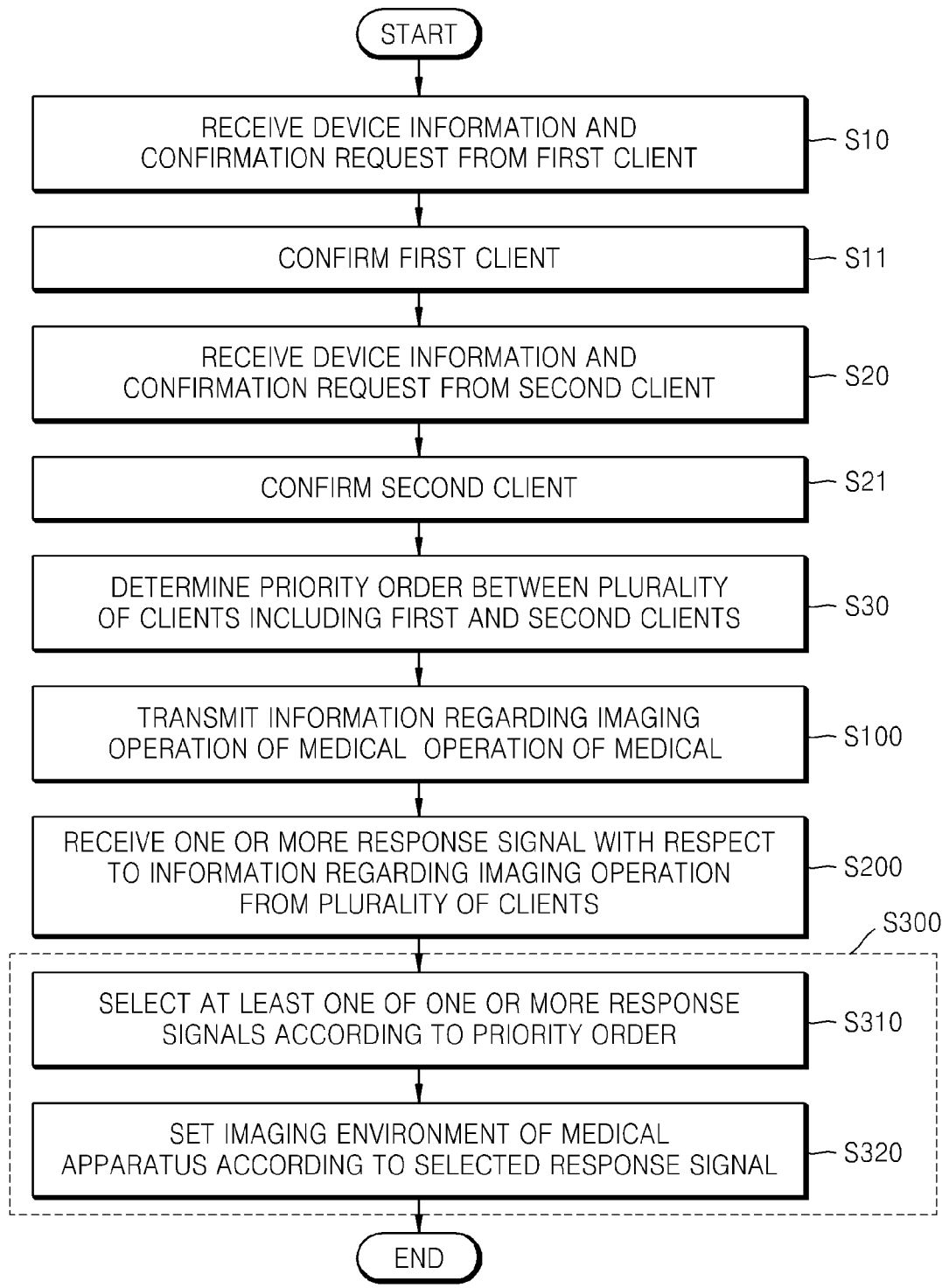
FIG. 10 is a flowchart illustrating a method of setting an imaging environment based on a response signal, according to an exemplary embodiment.

FIG. 10 is a diagram showing an example of setting an imaging environment based on a response signal, according to the exemplary embodiment.

The imaging environment setting apparatus 1000 according to the exemplary embodiment may receive device information about the first client 2000 and confirmation request from the first client 2000 (S10).

The device information about the first client 2000 may include an identifier of the first client 2000, and information about the user using the first client 2000. The information about the user using the first client 2000 may include an identification (ID) allocated to each user in advance, basic information of the user, profession of the user (for example, a doctor, a radiological technologist, a technician, etc.), and a position of the user.

The imaging environment setting apparatus 1000 may perform a confirmation process of the first client 2000 based on the device information of the first client 2000 (S11). For example, the imaging environment setting apparatus 1000 may determine whether the first client 2000 may access the imaging environment setting apparatus 1000 by using a database provided in a server 134 or an external storage (not shown). That is, the imaging environment setting apparatus 1000 may allow the first client 2000 to access thereto in a case where the device information of the first client 2000 coincides (matches) with the database that is provided in advance.

In addition, when the confirmation is finished, the imaging environment setting apparatus 1000 may transmit a confirmation complete signal notifying the allowance of access to the first client 2000.

Also, the imaging environment setting apparatus 1000 may receive device information about the second client 3000 and confirmation request from the second client 3000 (S20). Similarly to the above described process, the imaging environment setting apparatus 1000 may perform a confirmation process of the second client 3000 based on the device information of the second client 3000 (S21). In addition, when the confirmation is finished, the imaging environment setting apparatus 1000 may transmit a confirmation complete signal notifying allowance of the access to the second client 3000.

The imaging environment setting apparatus 1000 may determine a priority between the plurality of clients including the first and second clients 2000 and 3000 based on the information about the user using the first client 2000 and the information about the user using the second client 3000 (S30).

Since a responsible user (for example, one of the clinician, the radiological technologist, and the medical apparatus technician) is determined for each of the imaging processes of the object (for example, a imaging initiation process, an intermediate imaging process, a imaging complete process, etc.), and as described above, since the users may discuss through the video conference, there is a very small possibility of overlapping the response signals with each other from each of the users.

However, in each of the imaging initiation processes, the intermediate imaging process, and the imaging complete process, the response signals may be transmitted simultaneously from the plurality of users, and there is a need to determine a priority among the clients in order to process the response signals effectively.

The priority among the clients may be determined based on personal information of the users, professions of the users, and positions of the users using the first client 2000 and second client 3000 currently.

For example, if the clinician currently uses the first client 2000 and the radiological technologist or the medical apparatus technician currently uses the second client 3000, it may be determined that the first client 2000 has a higher priority than the second client 3000. That is, the priority order between the clients may be determined according to the users of the clients. For example, the priority order may be set in an order of the clinician, the radiological technologist, and the medical apparatus technician.

Also, the priority order between the clients may be vary depending on the information regarding the imaging operation. For example, with respect to the manipulation of the imaging parameters shown in FIGS. 4A and 4B, the priority may be determined in an order of the clinician, the radiological technologist, and the medical apparatus technician. Also, with respect to the manipulation of the image reconstruction method of FIG. 5, the priority may be determined in an order of the medical apparatus technician, the clinician, and the radiological technologist. Also, with respect to the manipulation of the auto tasking in FIG. 6, the priority may be determined in an order of the radiological technologist, the medical apparatus technician, and the clinician.

The imaging environment setting apparatus 1000 may transmit the information regarding the imaging operation of the medical apparatus to the first and second clines 2000 and 3000 (S100).

Also, the imaging environment setting apparatus 1000 may receive at least one response signal with respect to the information regarding the imaging operation from the plurality of clients 2000 and 3000 (S200).

For example, if the first client 2000 is used by the clinician and the second client 3000 is used by the radiological technologist, with respect to the image reconstruction method of FIG. 5, the clinician may want to reconstruct the image in the full mode and transmit a response signal for setting the full mode to the imaging environment setting apparatus 1000 and the radiological technologist may want to reconstruct the image in the plus mode and may transmit a response signal for setting the plus mode to the imaging environment setting apparatus 1000.

The imaging environment setting apparatus 1000 may select at least one from the at least one response signal according to the priority order determined between the plurality of clients 2000 and 3000 (S310).

In the above example, the imaging environment setting apparatus 1000 may select the response signal for setting the full mode according to the clinician's opinion having higher priority.

Also, the imaging environment setting apparatus 1000 may set the imaging environment of the medical apparatus according to the selected response signal (S320). In the above example, the imaging environment setting apparatus 1000 may set the image reconstruction type as a full mode according to the selected response signal for setting the full mode.

According to the exemplary embodiment, when receiving different response signals from the plurality of clients 2000 and 3000, the imaging environment setting apparatus 1000 may notify the plurality of clients 2000 and 3000 of the reception of the different response signals as a predetermined alarm.

For example, the predetermined alarm may be a message including at least one of characters, numbers, and graphical indicators (for example, icons). Also, the predetermined alarm may be provided to the user as sound or voice.

In the above example, with respect to the image reconstruction method of FIG. 5, if the clinician wants to reconstruct the captured image in the full mode and transmits a response signal for setting the full mode to the imaging environment setting apparatus 1000 and the radiological technologist wants to reconstruct the captured image in the plus mode and transmits a response signal for setting the plus mode to the imaging environment setting apparatus 1000, the imaging environment setting apparatus 1000 may notify the clinician and the radiological technologist of the reception of different response signals as a predetermined alarm.

For example, the imaging environment setting apparatus 1000 may transmit a message representing the response signal of the radiological technologist (for example, "the radiological technologist wants to reconstruct the image in the plus mode") to the clinician, and may transmit a message representing the response signal of the clinician (for example, "the clinician wants to reconstruct the image in the full mode") to the radiological technologist. The message may be provided to the user (for example, the clinician or the radiological technologist) as a pop-up on the display in each of the respective first client 2000 and second client 3000.

Therefore, the clinician or the radiological technologist may set the optical imaging environment by exchanging opinions through the imaging environment setting apparatus 1000.

Figure 11:
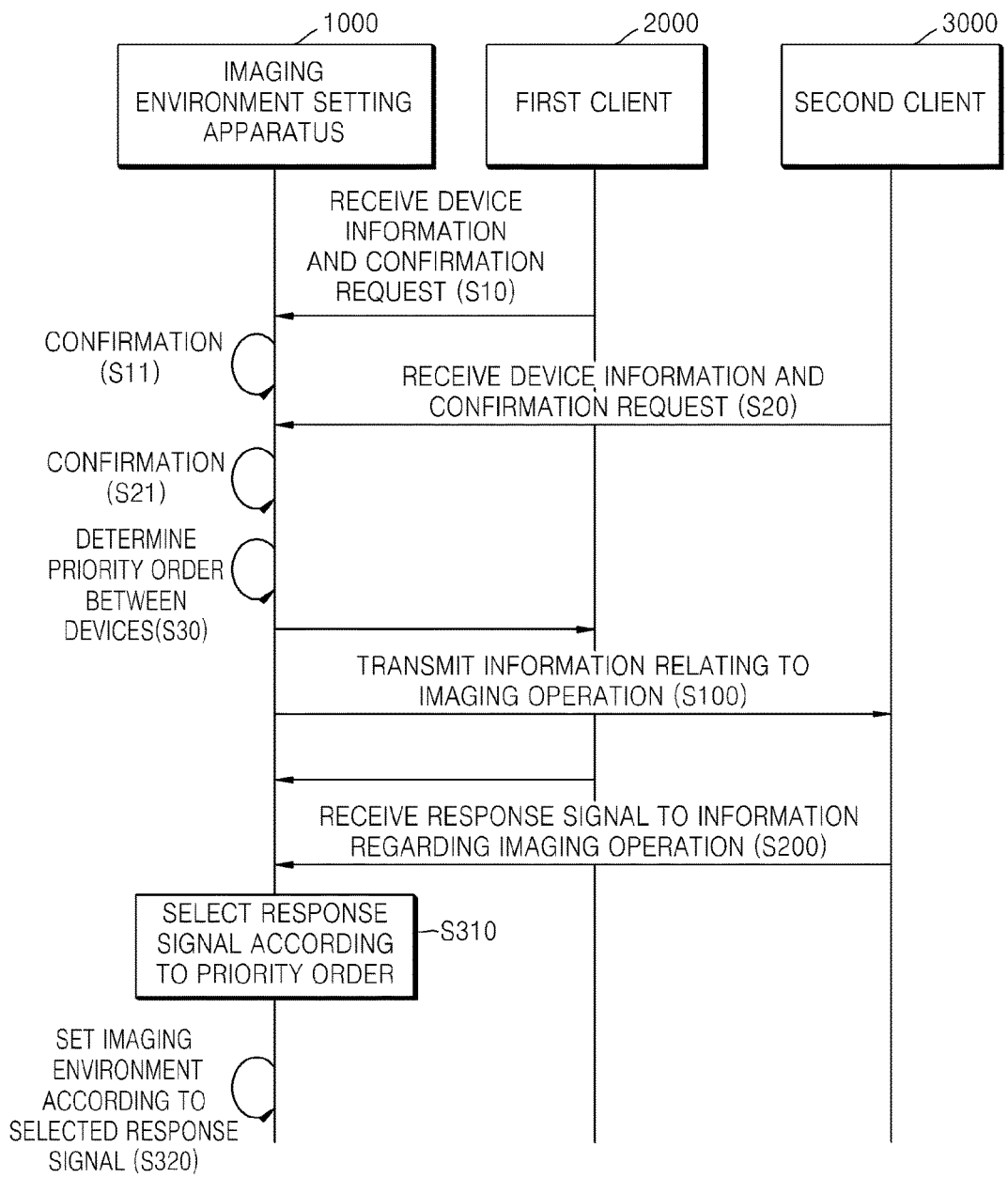
FIG. 11 is a timing diagram illustrating the method of setting the imaging environment of the medical apparatus based on connection confirmations of the plurality of clients and a priority order determined with respect to the plurality of confirmed clients, according to the exemplary embodiment.

FIG. 11 is a timing diagram illustrating a method of setting a imaging environment of a medical apparatus based on connection confirmations of the plurality of clients, and a priority order determined with respect to the plurality of confirmed clients, according to an exemplary embodiment.

FIG. 11 illustrates the same steps as that shown in FIG. 10 but in relation to the imaging environment setting apparatus 1000, the first client 2000 and the second client 3000. The imaging environment setting apparatus 1000 may receive the device information about the first client 2000 and the confirmation request from the first client 2000 (S10).

The imaging environment setting apparatus 1000 may perform a confirmation process for determining whether the access of the first client 2000 to the imaging environment setting apparatus 1000 is allowed by using the device information of the first client 2000 (S11). Also, the imaging environment setting apparatus 1000 may transmit the confirmation result to the first client 2000.

If the confirmation fails and the access of the first client 2000 to the imaging environment setting apparatus 1000 is denied, the first client 2000 updates the device information, and then, may transmit the updated device information and the confirmation request to the imaging environment setting apparatus 1000.

Also, the imaging environment setting apparatus 1000 may receive the device information about the second client 3000 and the confirmation request from the second client 3000 (S20), and may perform the confirmation process of the second client 3000 based on the device information of the second client 3000 (S21). In addition, the imaging environment setting apparatus 1000 may transmit the confirmation result to the second client 3000.

The imaging environment setting apparatus 1000 may determine a priority order between the first and second clients 2000 and 3000 based on the user information of the first client 2000 and the user information of the second client 3000 (S30).

The imaging environment setting apparatus 1000 may transmit the information relating to the imaging operation of the medical apparatus to the first and second clients 2000 and 3000 (S100).

Also, the imaging environment setting apparatus 1000 may receive at least one response signal with respect to the information relating to the imaging operation from the plurality of clients 2000 and 3000 (S200).

The imaging environment setting apparatus 1000 may select at least one of the response signal according to the priority order between the plurality of clients 2000 and 3000 (S310).

Then, the imaging environment setting apparatus 1000 may set the imaging environment of the medical apparatus according to the selected response signal (S320).

In addition, the imaging environment setting apparatus 1000 may transmit information representing the set imaging environment to the plurality of clients 2000 and 3000 in real-time as the information relating to the imaging operation. Thus, the plurality of clients 2000 and 3000 may identify the imaging environment setting in real-time.

Figure 12:
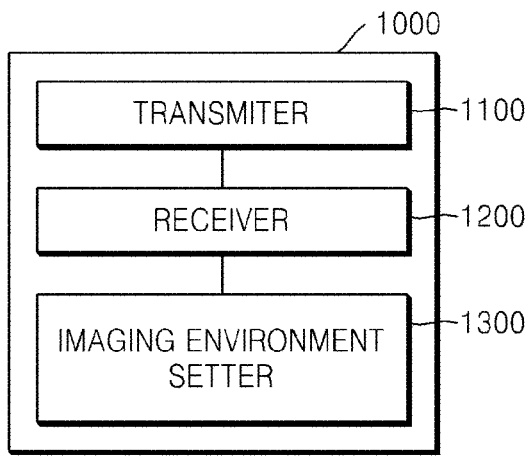
FIG. 12 is a block diagram of an apparatus for setting a imaging environment of a medical apparatus based on at least one signal transmitted from a plurality of clients, according to an exemplary embodiment.

FIG. 12 is a block diagram of a imaging environment setting apparatus 1000 for setting the imaging environment of a medical apparatus based on at least one signal transmitted from a plurality of clients, according to an exemplary embodiment.

The imaging environment setting apparatus 1000 according to the exemplary embodiment includes a transmitter 1100 transmitting information relating to a imaging operation of the medical apparatus to the plurality of clients 2000 and 3000, a receiver 1200 receiving at least one response signal with respect to the information relating to the imaging operation from the plurality of clients, and an imaging environment setter 1300 for setting the imaging environment of the medical apparatus based on the at least one response signal.

The information regarding the imaging operation may include at least one of image monitoring information, imaging parameter information, and image processing information.

The at least one response signal includes at least one of an image approval signal and a imaging termination signal as a response signal to the image monitoring information, a signal for changing the imaging parameter as a response signal to the imaging parameter information, and a signal for setting an image reconstruction condition as a response signal to the image processing information.

The information regarding the imaging operation may further include information about a video conference among the plurality of clients.

Also, the at least one response signal may include at least one of an image signal and a voice signal for the video conference.

The information representing the set imaging environment may be transmitted to the plurality of clients 2000 and 3000 via the transmitter 1100 as the information relating to the imaging operation. Imaging environment setting apparatus 1000 may be an apparatus included in a CT system 100 which will be described below with reference to FIG. 15, or may be a processor connected to the CT system 100.

Figure 13:
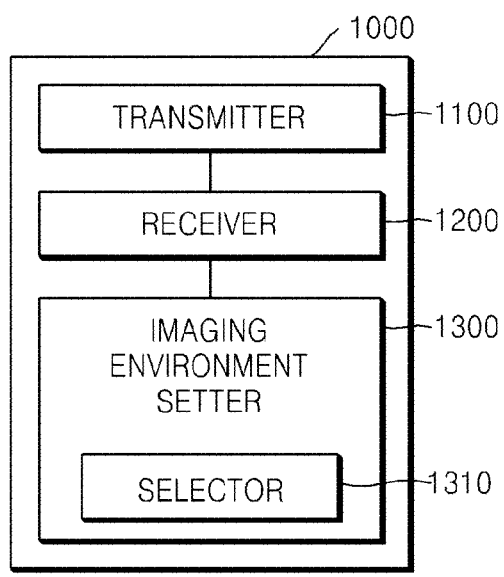
FIG. 13 is a block diagram of an apparatus for setting a imaging environment of a medical apparatus further including a selector, according to an exemplary embodiment.

FIG. 13 is a block diagram of an imaging environment setting apparatus 1000 further including a selector, according to an exemplary embodiment.

The imaging environment setter 1300 in the imaging environment setting apparatus 1000 may further include a selector for selecting at least one of one or more response signals according to a priority order between the plurality of clients. Also, the imaging environment setter 1300 may set the imaging environment of the medical apparatus according to the selected response signal.

Since a CT system is capable of providing a cross-sectional image of an object, the CT system may express an inner structure (e.g., an organ such as a kidney, a lung, etc.) of the object without any overlap with other organs, compared to a general X-ray capturing apparatus.

Since the CT system photographs the inner structure of the object by using X-rays, it is important to control an exposure dose of the object to radiation. Therefore, according to the exemplary embodiments, the imaging environment is set by using the signals transmitted from the plurality of clients, and thereby preventing a re-imaging operation that is not necessary and reduces the exposure dose of the object to radiation. That is, an optimal imaging environment suitable for the diagnosis of the object (for example, omission of unnecessary processes, and reduction in imaging time) may be set through the participations of the plurality of clients.

An exemplary CT system according to an exemplary embodiment will be described below.

The CT system 100 according to the exemplary embodiment will be described with reference to FIG. 14. The CT system 100 may include various devices.

Figure 14:
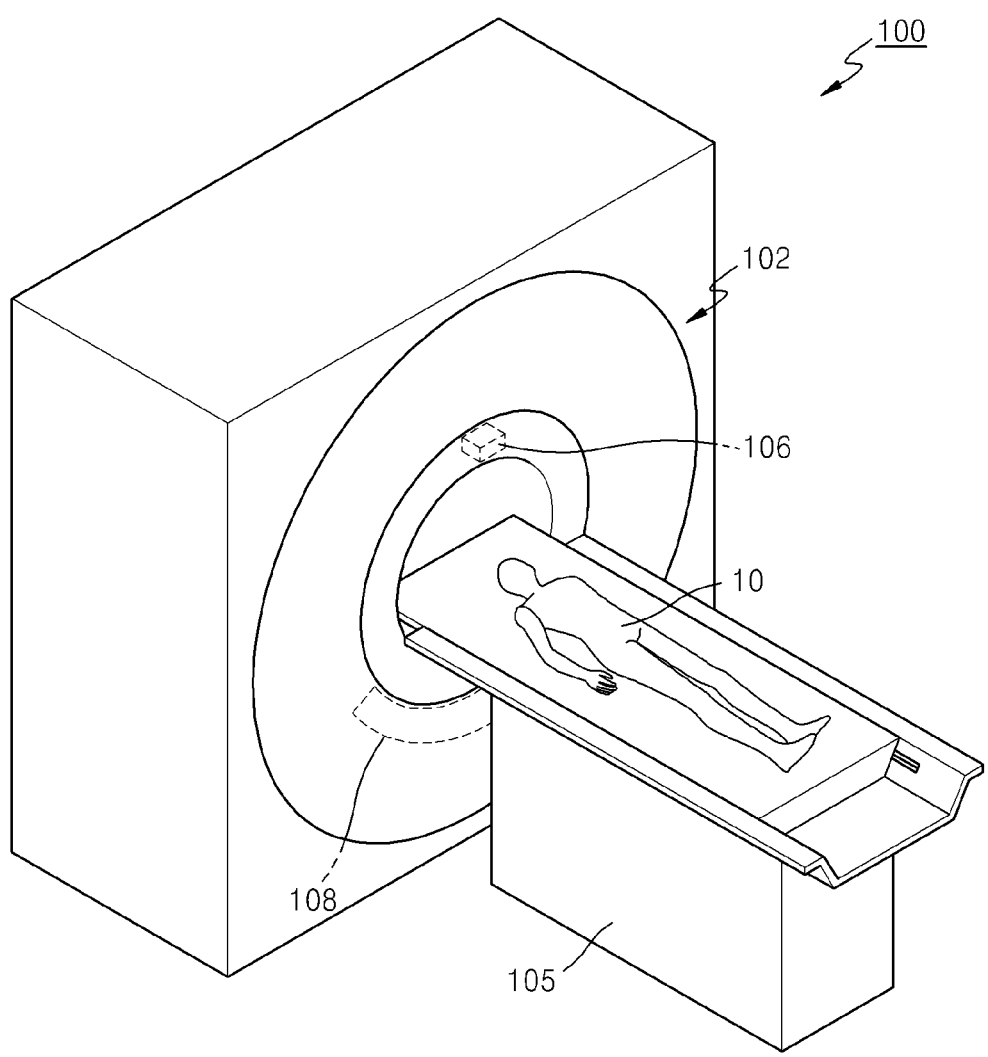
FIG. 14 is a schematic diagram of a computerized tomography (CT) system according to an exemplary embodiment.

FIG. 14 is a schematic diagram of the CT system 100. Referring to FIG. 14, the CT system 100 may include a gantry 102, a table 105, an X-ray generator 106, and an X-ray detector 108.

The gantry 102 may include the X-ray generator 106 and the X-ray detector 108.

A patient 10 may be positioned on the table 105.

The table 105 may move in a predetermined direction (e.g., at least one of up and down or right and left directions) during a CT imaging procedure. Also, the table 105 may tilt or rotate by a predetermined degree in a predetermined direction.

The gantry 102 may also tilt by a predetermined degree in a predetermined direction.

Figure 15:
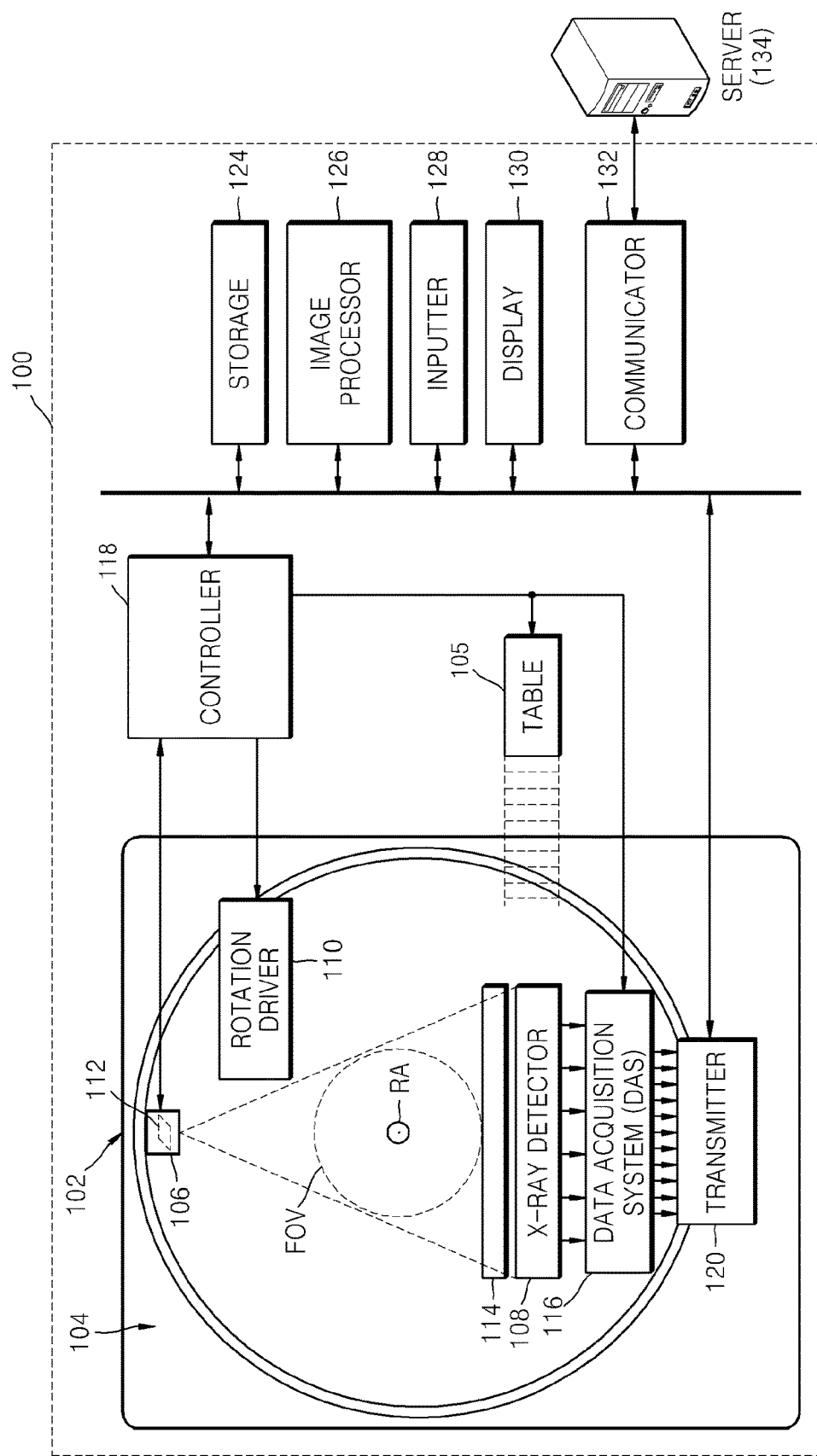
FIG. 15 is a block diagram exemplary showing a CT system according to an exemplary embodiment.

FIG. 15 is a diagram illustrating a structure of the CT system 100.

The CT system 100 may include the gantry 102, the table 105, a controller 118, a storage 124, an image processor 126, an inputter 128, a display 130, and a communicator 132.

As described above, the patient 10 may be positioned on the table 105. In the present exemplary embodiment, the table 105 may move in a predetermined direction (e.g., at least one of up and down or right and left directions), and movement of the table 105 may be controlled by the controller 118.

The gantry 102 may include a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. Also, the rotating frame 104 may have a disc shape.

The rotating frame 104 may include the X-ray generator 106 and the X-ray detector 108 that face each other so as to have a predetermined field of view FOV. The rotating frame 104 may also include an anti-scatter grid 114. The anti-scatter grid 114 may be positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates a quality of an image. In order to transmit the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 by a predetermined rotation speed. The rotating frame 104 may receive the driving signal and power from the rotation driver 110 while the rotating frame 104 contacts the rotation driver 110 via a slip ring (not shown). Also, the rotating frame 104 may receive the driving signal and power from the rotation driver 110 via wireless communication.

The X-ray generator 106 may receive a voltage and current from a power distribution unit (PDU) (not shown) via a slip ring (not shown) and then a high voltage generator (not shown), and then may generate and emit X-rays. When the high voltage generator applies predetermined voltage (hereinafter, referred as the tube voltage) to the X-ray generator 106, the X-ray generator 106 may generate X-rays having a plurality of energy spectrums that correspond to the tube voltage.

The X-rays generated by the X-ray generator 106 may be shaped into a predetermined form by a collimator 112.

The X-ray detector 108 may be positioned to face the X-ray generator 106. The X-ray detector 108 may include a plurality of X-ray detecting devices. Each of the plurality of X-ray detecting devices may establish one channel but one or more exemplary embodiments are not limited thereto.

The X-ray detector 108 may detect the X-rays generated by the X-ray generator 106 and transmitted via the patient 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. The electrical signal generated by the X-ray detector 108 may be wiredly or wirelessly collected by the DAS 116. Also, the electrical signal generated by the X-ray detector 108 may be provided to an analog-to-digital converter (not shown) via an amplifier (not shown).

According to a slice thickness or the number of slices of the object being imaged, only some of a plurality of data collected by the X-ray detector 108 may be provided to the image processor 126 via the data transmitter 120, or the image processor 126 may select only some of the plurality of data. A slice can be, for example, a component of the object being imaged and object can be divided into multiple slices during imaging.

The digital signal may be provided to the image processor 126 via the data transmitter 120. The digital signal may also be wiredly or wirelessly provided to the image processor 126.

The controller 118 may control an operation of each of modules in the CT system 100. For example, the controller 118 may control operations of the table 105, the rotation driver 110, the collimator 112, the DAS 116, the storage 124, the image processor 126, the inputter 128, the display 130, the communicator 132, or the like.

The image processor 126 may receive data (e.g., pure data before a processing operation), which is obtained from the DAS 116, via the data transmitter 120, and may perform pre-processing.

The pre-processing may include a process of correcting sensitivity irregularity between channels, a process of correcting a signal loss due to a rapid decrease of a signal intensity or due to an X-ray absorbing material such as metal or the like.

Data output from the image processor 126 may be referred to as raw data or projection data. The projection data and image-capturing conditions (e.g., the tube voltage, an image-capturing angle, etc.) while the data is being obtained may be stored together in the storage 124.

The projection data may be a group of data values that correspond to the intensity of the X-ray that passes through the object 10. For convenience of description, it is assumed that a group of a plurality of pieces of projection data that are simultaneously obtained from all channels by a same image-capturing degree is referred as a projection data set.

The storage 124 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable Read-Only Memory (EEPROM), Programmable Read-Only Memory (PROM) magnetic memory, a magnetic disc, and an optical disc.

The image processor 126 may reconstruct a cross-sectional image with respect to the patient 10 by using the projection data set. The cross-sectional image may be a 3D image. In other words, the image processor 126 may reconstruct the 3D image of the object 10 by using a cone beam reconstruction method or the like, based on the projection data set.

The inputter 128 may receive an external input with respect to an X-ray tomography imaging condition, an image processing condition, or the like. For example, the X-ray tomography imaging condition may include tube voltages, energy value setting with respect to a plurality of X-rays, selection of an image-capturing protocol, selection of an image reconstruction method, setting of a FOV area, the number of slices, a slice thickness, parameter setting with respect to image post-processing, or the like. Also, the image processing condition may include a resolution of an image, attenuation coefficient setting with respect to the image, setting of an image combining ratio, or the like.

The inputter 128 may include a device for receiving a predetermined input from an external source. For example, the inputter 128 may include a microphone, a keyboard, a mouse, a joystick, a touch pad, a touch pen, a voice recognition device, a gesture recognition device, or the like.

The display 130 may display an X-ray tomography image reconstructed by the image processor 126.

Exchanges of data, power, or the like between the aforementioned elements may be performed by using at least one of wired communication, wireless communication, and optical communication.

The communicator 132 may perform communication with an external device, an external medical apparatus, etc. via a server 134 or the like. The communication will now be described with reference to FIG. 16.

Figure 16:
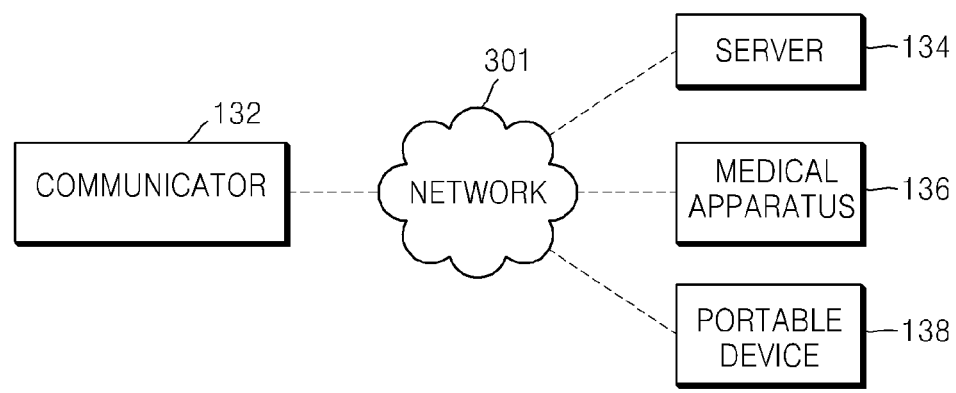
FIG. 16 is an exemplary diagram of a communicator according to an exemplary embodiment.

FIG. 16 is a diagram illustrating a structure of the communicator 132.

The communicator 132 may be wiredly or wirelessly connected to a network 301 and therefore may perform communication with the server 134, an external medical apparatus 136, or an external portable device 138. The communicator 132 may exchange data with a hospital server or other medical apparatuses in a hospital connected via a Picture Archiving and Communication System (PACS).

Also, the communicator 132 may perform data communication with the portable device 138 or the like according to a Digital Imaging and Communications in Medicine (DICOM) standard.

The communicator 132 may transmit and receive data for diagnosing the patient 10 via the network 301. Also, the communicator 132 may transmit and receive a medical image obtained from the medical apparatus 136 such as a magnetic resonance imaging (MRI) apparatus, an X-ray apparatus, or the like.

Furthermore, the communicator 132 may receive a diagnosis history or a medical treatment schedule of a patient from the server 134 and may use the diagnosis history or the medical treatment schedule for a clinical diagnosis of the patient. Also, the communicator 132 may perform data communication not only with the server 134 or the medical apparatus 136 in a hospital but also with the portable device 138 of a user or patient.

Also, the communicator 132 may transmit information about a device error, information about a quality control status, or the like to a system manager or a service manager via the network 301, and may receive feedback corresponding to the information.

The above descriptions may also apply to an apparatus according to the exemplary embodiments. Therefore, the same components of the apparatus as those in the above descriptions are omitted here.

The exemplary embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more exemplary embodiments have been described with reference to the figures, it will be understood by those of ordinary skill in the art that various changes in form and details may be made therein without departing from the spirit and scope as defined by the following claims.

What is claimed is:

1. A method of setting an imaging environment of a medical apparatus based on one or more signals transmitted from a plurality of clients, the method comprising:
    transmitting information regarding an imaging operation of the medical apparatus to the plurality of clients;
    receiving one or more response signals with respect to the information from the plurality of clients;
    selecting a response signal from among one or more response signals according to a priority order between the plurality of clients; and
    setting the imaging environment of the medical apparatus based on the selected response signal.

2. The method of claim 1, wherein the selecting comprises selecting the response signal according to a client which has higher priority.

3. The method of claim 1, wherein the priority order between the plurality of clients is determined based on at least one of personal information of a plurality of users, professions of the plurality of users, and positions of the plurality of users corresponding to the plurality of clients.

4. The method of claim 1, further comprising:
    when receiving different response signals with respect to the information from the plurality of clients, notifying the plurality of clients of reception of the different response signals as a predetermined alarm.

5. The method of claim 1, further comprising:
    when receiving different response signals with respect to the information from the plurality of clients, transmitting a message representing the response signal of one of the plurality of clients to other clients.

6. The method of claim 1, wherein the information regarding the imaging operation comprises at least one of image monitoring information, imaging parameter information, and image processing information.

7. The method of claim 6, wherein the one or more response signals comprise at least one of an imaging approval signal or an imaging termination signal if the information related to the imaging operation is the image monitoring information, a signal to change imaging parameters if the information related to the imaging operation is the imaging parameter information, and a signal to set an image reconstruction condition if the information related to the imaging operation is the image processing information.

8. The method of claim 6, wherein the information relating to the imaging operation further comprises information about a video conference between the plurality of clients.

9. The method of claim 8, wherein the one or more response signals comprise at least one of an image signal and a voice signal for the video conference.

10. The method of claim 1, wherein information representing the set imaging environment is transmitted to the plurality of clients in real-time by transmitting information regarding the imaging operation.

11. An apparatus for setting an imaging environment of a medical apparatus based on one or more response signals transmitted from a plurality of clients, the apparatus comprising:
    at least one memory storing instructions; and
    at least one processor configured to execute the stored instructions to:
        transmit information regarding an imaging operation of the medical apparatus to the plurality of clients;
        receive the one or more response signals with respect to the information from the plurality of clients;
        select a response signal from among one or more response signals according to a priority order between the plurality of clients; and
        set the imaging environment of the medical apparatus based on the one or more response signals.

12. The apparatus of claim 11, wherein the at least one processor is configured to execute the stored instructions to:
    select the response signal according to a client which has higher priority.

13. The apparatus of claim 11, wherein the priority order between the plurality of clients is determined based on at least one of personal information of a plurality of users, professions of the plurality of users, and positions of the plurality of users corresponding to the plurality of clients.

14. The apparatus of claim 11, wherein the at least one processor is configured to execute the stored instructions to:
    when receiving different response signals with respect to the information from the plurality of clients, notify the plurality of clients of reception of the different response signals as a predetermined alarm.

15. The apparatus of claim 11, wherein the at least one processor is configured to execute the stored instructions to:
    when receiving different response signals with respect to the information from the plurality of clients, transmit a message representing the response signal of one of the plurality of clients to other clients.

16. The apparatus of claim 11, wherein the information relating to the imaging operation comprises at least one of image monitoring information, imaging parameter information, and image processing information.

17. The apparatus of claim 16, wherein the one or more response signals comprises at least one of an imaging approval signal or an imaging termination signal if the information related to the imaging operation is the image monitoring information, a signal to change the imaging parameters if the information related to the imaging operation is the imaging parameter information, and a signal to set an image reconstruction condition if the information related to the imaging operation is the image processing information.

18. The apparatus of claim 16, wherein the information regarding the imaging operation further comprises information about a video conference between the plurality of clients.

19. The apparatus of claim 18, wherein the one or more response signals comprise at least one of an image signal and a voice signal for the video conference.

20. A non-transitory computer readable recording medium having embodied thereon a program for executing a method for setting an imaging environment of a medical apparatus based on one or more signals transmitted from a plurality of clients, the method comprising:
   transmitting information regarding an imaging operation of the medical apparatus to the plurality of clients;
   receiving one or more response signals with respect to the information from the plurality of clients;
   selecting a response signal from among one or more response signals according to a priority order between the plurality of clients; and
   setting the imaging environment of the medical apparatus based on the selected response signal.

* * * * *